(12) United States Patent
    Hunter

(10) Patent No.: US 11,998,348 B2
(45) Date of Patent: Jun. 4, 2024

(54) DEVICES, SYSTEMS AND METHODS FOR USING AND MONITORING HEART VALVES

(71) Applicant: Canary Medical Inc., Vancouver (CA)

(72) Inventor: William L. Hunter, Vancouver (CA)

(73) Assignee: Canary Medical Switzerland AG, Baar (CH)

( * ) Notice: Subject to any disclaimer, the term of this patent is extended or adjusted under 35 U.S.C. 154(b) by 198 days.

(21) Appl. No.: 16/777,713

(22) Filed: Jan. 30, 2020

(65) Prior Publication Data

US 2020/0268316 A1   Aug. 27, 2020

Related U.S. Application Data

(63) Continuation of application No. 15/320,296, filed as application No. PCT/US2015/037810 on Jun. 25, 2015, now abandoned.
(Continued)

(51) Int. Cl.
    *A61B 5/00*     (2006.01)
    *A61B 5/0205*   (2006.01)
    *A61B 5/0215*   (2006.01)
    *A61B 5/026*    (2006.01)
    *A61B 5/145*    (2006.01)
    *A61F 2/24*     (2006.01)
    *G16B 40/00*    (2019.01)
    (Continued)

(52) U.S. Cl.
    CPC .......... *A61B 5/4851* (2013.01); *A61B 5/0022* (2013.01); *A61B 5/0024* (2013.01); *A61B 5/0028* (2013.01); *A61B 5/0031* (2013.01); *A61B 5/02055* (2013.01); *A61B 5/686* (2013.01); *A61B 5/6869* (2013.01); *A61F 2/2472* (2013.01); *G16B 40/00* (2019.02); *G16B 40/10* (2019.02); *G16H 40/67* (2018.01); *A61B 5/0215* (2013.01); *A61B 5/026* (2013.01); *A61B 5/1102* (2013.01); *A61B 5/14542* (2013.01); *A61B 2560/0219* (2013.01); *A61B 2562/0219* (2013.01); *A61B 2562/0247* (2013.01); *A61B 2562/0261* (2013.01); *A61F 2/2412* (2013.01); *A61F 2/2418* (2013.01); *A61F 2/2427* (2013.01); *A61F 2/2433* (2013.01); *A61F 2250/0002* (2013.01); *A61F 2250/0096* (2013.01); *G16H 40/63* (2018.01)

(58) Field of Classification Search
    CPC ....................................................... A61B 5/686
    See application file for complete search history.

(56) References Cited

U.S. PATENT DOCUMENTS

4,077,030 A   2/1978  Helava
4,103,337 A   7/1978  Whiteside
(Continued)

FOREIGN PATENT DOCUMENTS

CN    1709210 A    12/2005
CN    101043859 A   9/2007
(Continued)

OTHER PUBLICATIONS

PCT International Search Report and Written Opinion dated May 9, 2014, for PCT/US2013/077356.
(Continued)

*Primary Examiner* — Jacqueline Woznicki

(57) ABSTRACT

Heart valves are provided, comprising a heart valve and a plurality of sensors.

21 Claims, 19 Drawing Sheets

Related U.S. Application Data

(60) Provisional application No. 62/017,161, filed on Jun. 25, 2014.

(51) Int. Cl.
*G16B 40/10* (2019.01)
*G16H 40/67* (2018.01)
*A61B 5/11* (2006.01)
*G16H 40/63* (2018.01)

(56) References Cited

U.S. PATENT DOCUMENTS

| | | |
|---|---|---|
| 4,769,032 A | 9/1988 | Steinberg |
| 5,487,760 A | 1/1996 | Villafana |
| 5,591,227 A | 1/1997 | Dinh et al. |
| 5,672,954 A | 9/1997 | Watanabe |
| 5,716,981 A | 2/1998 | Hunter et al. |
| 5,749,824 A | 5/1998 | Guth |
| 5,779,729 A | 7/1998 | Severini |
| 5,833,603 A | 11/1998 | Kovacs et al. |
| 6,053,873 A | 4/2000 | Govari et al. |
| 6,123,722 A | 9/2000 | Fogarty et al. |
| 6,206,835 B1 | 3/2001 | Spillman, Jr. et al. |
| 6,331,163 B1 | 12/2001 | Kaplan |
| 6,387,124 B1 | 5/2002 | Buscemi et al. |
| 6,398,734 B1 | 6/2002 | Cimochowski et al. |
| 6,447,448 B1 | 9/2002 | Ishikawa et al. |
| 6,610,101 B2 | 8/2003 | Herr et al. |
| 6,706,071 B1 | 3/2004 | Wolter |
| 6,712,778 B1 | 3/2004 | Jeffcoat et al. |
| 6,852,153 B2 | 2/2005 | Uhlir-Tsang et al. |
| 6,869,443 B2 | 3/2005 | Buscemi et al. |
| 7,011,678 B2 | 3/2006 | Tenerz et al. |
| 7,025,778 B2 | 4/2006 | Hayashi et al. |
| 7,044,981 B2 | 5/2006 | Liu et al. |
| 7,123,700 B1 | 10/2006 | Mazar |
| 7,127,300 B2 | 10/2006 | Mazar et al. |
| 7,147,604 B1* | 12/2006 | Allen ............... A61B 5/0031 |
| | | 600/549 |
| 7,179,289 B2 | 2/2007 | Shanley |
| 7,208,010 B2 | 4/2007 | Shanley et al. |
| 7,248,923 B2 | 7/2007 | Maile et al. |
| 7,294,145 B2 | 11/2007 | Ward |
| 7,377,937 B2 | 5/2008 | Dolan |
| 7,383,071 B1 | 6/2008 | Russell et al. |
| 7,416,530 B2 | 8/2008 | Turner et al. |
| 7,452,334 B2 | 11/2008 | Gianchandani et al. |
| 7,491,188 B2 | 2/2009 | Holman et al. |
| 7,553,923 B2 | 6/2009 | Williams et al. |
| 7,643,879 B2* | 1/2010 | Shuros ............... A61N 1/39622 |
| | | 607/18 |
| 7,691,141 B2 | 4/2010 | Lewis et al. |
| 7,806,917 B2 | 10/2010 | Xiao |
| 7,813,808 B1 | 10/2010 | Doron et al. |
| 7,879,082 B2 | 2/2011 | Brown |
| 7,914,568 B2 | 3/2011 | Cully et al. |
| 7,942,923 B2 | 5/2011 | Gregorich |
| 7,996,058 B2 | 8/2011 | Ben-Haim et al. |
| 8,001,925 B2 | 8/2011 | Kantor |
| 8,003,157 B2 | 8/2011 | Andreacchi et al. |
| 8,080,051 B2 | 12/2011 | Lewis et al. |
| 8,100,960 B2 | 1/2012 | Bruszewski |
| 8,123,799 B1 | 2/2012 | Malik et al. |
| 8,277,833 B2 | 10/2012 | Atanasoska et al. |
| 8,277,867 B2 | 10/2012 | Fredrickson et al. |
| 8,283,793 B2 | 10/2012 | Pless |
| 8,287,588 B2 | 10/2012 | Leynov et al. |
| 8,308,794 B2 | 11/2012 | Martinson et al. |
| 8,311,632 B2 | 11/2012 | Pless et al. |
| 8,480,612 B2 | 7/2013 | Kassem |
| 8,562,671 B2 | 10/2013 | Neuenschwander |
| 8,568,474 B2 | 10/2013 | Yeung et al. |
| 8,852,571 B2 | 10/2014 | Pittenger et al. |
| 9,949,692 B2 | 4/2018 | Hunter |
| 10,499,855 B2 | 12/2019 | Hunter |
| 10,542,931 B2 | 1/2020 | Kuraguntla |
| 2002/0088517 A1 | 7/2002 | Shimura |
| 2002/0128546 A1 | 9/2002 | Silver |
| 2003/0104030 A1 | 6/2003 | Igaki et al. |
| 2003/0204245 A1 | 10/2003 | Brightbill |
| 2003/0229388 A1 | 12/2003 | Hayashi et al. |
| 2004/0102733 A1* | 5/2004 | Naimark ............... A61B 5/145 |
| | | 604/65 |
| 2004/0116822 A1 | 6/2004 | Lindsey |
| 2004/0193021 A1 | 9/2004 | Zdeblick |
| 2004/0199241 A1 | 10/2004 | Gravett et al. |
| 2005/0021126 A1 | 1/2005 | Machan et al. |
| 2005/0051871 A1 | 3/2005 | Lowther et al. |
| 2005/0065592 A1 | 3/2005 | Holzer |
| 2005/0082351 A1* | 4/2005 | Pinchot ............... B01J 19/0093 |
| | | 228/215 |
| 2005/0102026 A1 | 5/2005 | Turner et al. |
| 2005/0149170 A1 | 7/2005 | Tassel et al. |
| 2005/0149173 A1 | 7/2005 | Hunter et al. |
| 2005/0152945 A1 | 7/2005 | Hunter et al. |
| 2005/0165317 A1* | 7/2005 | Turner ............... A61B 5/0031 |
| | | 623/1.1 |
| 2005/0171594 A1 | 8/2005 | Machan et al. |
| 2005/0177103 A1 | 8/2005 | Hunter et al. |
| 2005/0181004 A1 | 8/2005 | Hunter et al. |
| 2005/0181005 A1 | 8/2005 | Hunter et al. |
| 2005/0181009 A1 | 8/2005 | Hunter et al. |
| 2005/0181011 A1 | 8/2005 | Hunter et al. |
| 2005/0186242 A1 | 8/2005 | Hunter et al. |
| 2005/0187639 A1 | 8/2005 | Hunter et al. |
| 2005/0242666 A1 | 11/2005 | Huscher et al. |
| 2005/0267569 A1 | 12/2005 | Barrett et al. |
| 2006/0055088 A1 | 3/2006 | Nakayashiki et al. |
| 2006/0079740 A1* | 4/2006 | Silver ............... A61B 5/6882 |
| | | 600/353 |
| 2006/0079836 A1 | 4/2006 | Holman et al. |
| 2006/0122522 A1 | 6/2006 | Chavan et al. |
| 2006/0129050 A1 | 6/2006 | Martinson et al. |
| 2006/0155358 A1 | 7/2006 | LaDuca et al. |
| 2006/0192214 A1 | 8/2006 | Ogihara et al. |
| 2007/0173861 A1 | 7/2007 | Strommer et al. |
| 2007/0225802 A1 | 9/2007 | Forsell |
| 2007/0234819 A1 | 10/2007 | Amirouche et al. |
| 2007/0238984 A1 | 10/2007 | Maschke et al. |
| 2007/0270940 A1 | 11/2007 | Doty |
| 2008/0021307 A1 | 1/2008 | Freeman et al. |
| 2008/0033527 A1 | 2/2008 | Nunez et al. |
| 2008/0051838 A1 | 2/2008 | Shuros et al. |
| 2008/0065225 A1 | 3/2008 | Wasielewski et al. |
| 2008/0071315 A1* | 3/2008 | Baynham ............ A61N 1/36514 |
| | | 607/9 |
| 2008/0088436 A1 | 4/2008 | Reeves et al. |
| 2008/0109051 A1 | 5/2008 | Splinter et al. |
| 2008/0139954 A1 | 6/2008 | Day et al. |
| 2008/0176271 A1 | 7/2008 | Silver et al. |
| 2008/0215609 A1 | 9/2008 | Cleveland et al. |
| 2008/0275350 A1 | 11/2008 | Liao et al. |
| 2008/0294019 A1 | 11/2008 | Tran |
| 2008/0300597 A1 | 12/2008 | Morgan et al. |
| 2008/0300659 A1 | 12/2008 | Matos |
| 2009/0119222 A1 | 5/2009 | Kevin |
| 2009/0131767 A1 | 5/2009 | Arne et al. |
| 2009/0192588 A1 | 7/2009 | Shin et al. |
| 2009/0227883 A1 | 9/2009 | Zhang et al. |
| 2009/0254063 A1 | 10/2009 | Oepen et al. |
| 2009/0292222 A1 | 11/2009 | Ferren et al. |
| 2010/0023108 A1 | 1/2010 | Toner et al. |
| 2010/0042121 A1 | 2/2010 | Schneider et al. |
| 2010/0117471 A1 | 5/2010 | Huang |
| 2010/0152621 A1 | 6/2010 | Janna |
| 2010/0217136 A1 | 8/2010 | Turner et al. |
| 2010/0285082 A1 | 11/2010 | Fernandez |
| 2010/0298895 A1* | 11/2010 | Ghaffari ............... A61B 5/02028 |
| | | 607/116 |
| 2011/0046452 A1 | 2/2011 | Najafi et al. |
| 2011/0054583 A1 | 3/2011 | Litt et al. |
| 2011/0059234 A1 | 3/2011 | Byun et al. |
| 2011/0063094 A1 | 3/2011 | Meiertoberens et al. |

(56) References Cited

U.S. PATENT DOCUMENTS

| | | | |
|---|---|---|---|
| 2011/0092948 A1 | 4/2011 | Shachar et al. | |
| 2011/0092955 A1* | 4/2011 | Purdy | A61B 5/6852 604/523 |
| 2011/0264194 A1* | 10/2011 | Griswold | A61B 5/6862 600/300 |
| 2012/0123284 A1 | 5/2012 | Kheradvar | |
| 2013/0041454 A1 | 2/2013 | Dobson et al. | |
| 2013/0058556 A1 | 3/2013 | Ohishi et al. | |
| 2013/0109998 A1 | 5/2013 | Swoboda | |
| 2013/0166023 A1 | 6/2013 | Pipenhagen | |
| 2013/0252610 A1 | 9/2013 | Kim et al. | |
| 2013/0281839 A1 | 10/2013 | Yan et al. | |
| 2014/0031063 A1 | 1/2014 | Park et al. | |
| 2014/0048970 A1 | 2/2014 | Batchelder et al. | |
| 2014/0081154 A1 | 3/2014 | Toth | |
| 2014/0085102 A1 | 3/2014 | McCormick | |
| 2014/0144070 A1 | 5/2014 | Waterson et al. | |
| 2014/0256324 A1 | 9/2014 | Mohanty et al. | |
| 2014/0257047 A1 | 9/2014 | Sillay et al. | |
| 2014/0328253 A1 | 11/2014 | Lee et al. | |
| 2015/0112188 A1 | 4/2015 | Stigall | |
| 2015/0335290 A1 | 11/2015 | Hunter | |
| 2016/0029952 A1 | 2/2016 | Hunter | |
| 2016/0038087 A1 | 2/2016 | Hunter | |
| 2016/0192878 A1 | 7/2016 | Hunter | |
| 2016/0340177 A1 | 11/2016 | Takada | |
| 2017/0138986 A1 | 5/2017 | Kern | |
| 2017/0181825 A1 | 6/2017 | Hunter | |
| 2017/0189553 A1 | 7/2017 | Hunter | |
| 2017/0196478 A1 | 7/2017 | Hunter | |
| 2017/0196499 A1 | 7/2017 | Hunter | |
| 2017/0196508 A1 | 7/2017 | Hunter | |
| 2017/0196509 A1 | 7/2017 | Hunter | |
| 2017/0328931 A1 | 11/2017 | Zhang et al. | |
| 2018/0235546 A1 | 8/2018 | Hunter | |
| 2019/0060003 A1* | 2/2019 | Tuason | A61B 34/20 |
| 2019/0076033 A1 | 3/2019 | Sweeney et al. | |
| 2020/0289060 A1 | 9/2020 | Hunter | |

FOREIGN PATENT DOCUMENTS

| | | |
|---|---|---|
| CN | 101094622 A | 12/2007 |
| CN | 101188984 A | 5/2008 |
| CN | 101484070 A | 7/2009 |
| CN | 101557777 A | 10/2009 |
| GB | 2379882 A | 3/2003 |
| JP | 2004532051 A | 10/2004 |
| JP | 2007083019 A | 4/2007 |
| JP | 2007515195 A | 6/2007 |
| JP | 2008237642 A | 10/2008 |
| JP | 2009542421 A | 12/2009 |
| WO | 9836709 A1 | 8/1998 |
| WO | 2002064019 A2 | 8/2002 |
| WO | 2005046467 A1 | 5/2005 |
| WO | 2006029364 A2 | 3/2006 |
| WO | 2006055443 A3 | 5/2007 |
| WO | 2007057739 A1 | 5/2007 |
| WO | 2008006003 A2 | 1/2008 |
| WO | 2008024180 A1 | 2/2008 |
| WO | 2012011108 A2 | 1/2012 |
| WO | 2012061825 A2 | 5/2012 |
| WO | 2012170837 A2 | 12/2012 |
| WO | 2013044160 A2 | 3/2013 |
| WO | 2014144107 | 3/2014 |
| WO | 2014100795 | 6/2014 |
| WO | 2014100795 A1 | 6/2014 |
| WO | 2014209916 | 6/2014 |
| WO | 2014144070 | 9/2014 |
| WO | 2014144070 A1 | 9/2014 |
| WO | 2015200704 | 6/2015 |
| WO | 2015200707 | 6/2015 |
| WO | 2015200707 A1 | 6/2015 |
| WO | 2015200718 | 6/2015 |
| WO | 2015200720 | 6/2015 |
| WO | 2015200722 | 12/2015 |
| WO | 2015200723 | 12/2015 |

OTHER PUBLICATIONS

PCT International Search Report and Written Opinion dated Jul. 8, 2014, for PCT/US2014/028323.

PCT International Search Report and Written Opinion dated Oct. 7, 2015, for PCT/US2015/037810.

European Partial Search Report dated Oct. 24, 2016, for 14762269.0.

European Partial Search Report dated Feb. 16, 2018, for 15811456.1.

Bonsignore, Craig S., "Open Stent Design: Design and analysis of self expanding cardiovascular stents", CreateSpace Independent Publishing Platform, Nov. 2012.

Chandrakasan et al., "Next Generation Micro-Power Systems", 2008 Symposium on VLSI Circuits Digest of Technical Papers, pp. 1-5.

Loh, N.C. et al., "Sub-10 cm3 Intererometric Accelerometer with Nano-g Resolution", J. Microelectromechanical Sys., 11:3, Jun. 2002, pp. 182-187.

Polla, D.L. et al., "Microdevices in Medicine", Ann. Rev. Biomed. Eng., 2000, 02:551-576.

Singh, U.K. et al., "Piezoelectric Power Scavenging of Mechanical Vibration Energy", Australian Mining Technology Conference, October 204, 2007, pp. 111-118.

Yeh, R. et al., "Single Mask, Large Force, and Large Displacement Electrostatic Linear Inchworm Motors", J. Microelectromechanical Sys,. 11:4, Aug. 2002, pp. 330-336.

Yun, K.S. et al., "A Surface-Tension Driven Micropump for Low-voltage and Low-power Operations", J. Microelectromechanical Sys., 11:5, Oct. 2002, pp. 454-461.

Kroft, Steve, "The Data Brokers: Selling your Personal Information" pp. 1-8, extracted from Google on Sep. 4, 2014 is a script from "The Data Brokers" aired on Mar. 9, 2014 on 60 Minutes CBS.

Extended European Search Report for European Application No. 21200224.0, dated Mar. 23, 2022, 08 Pages.

Extended European Search Report for European Application No. 15811456.1, dated Jul. 9, 2018, 13 Pages.

International Preliminary Report on Patentability for International Application No. PCT/US2013/077356, dated Jul. 2, 2015, 10 Pages.

International Preliminary Report on Patentability for International Application No. PCT/US2014/028323, dated Sep. 24, 2015, 13 Pages.

* cited by examiner

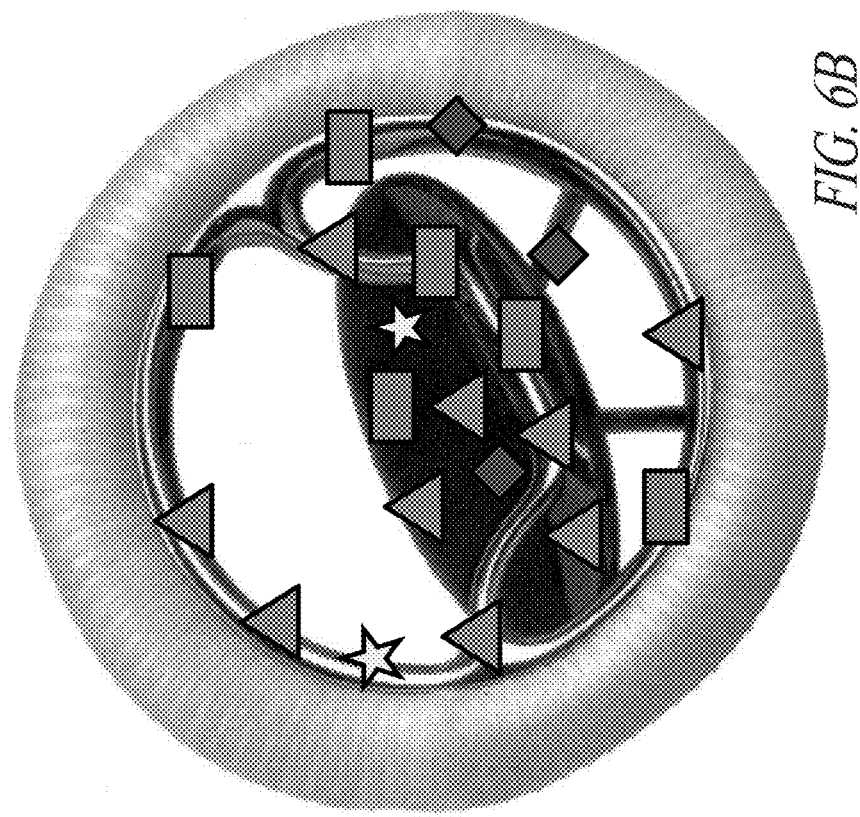
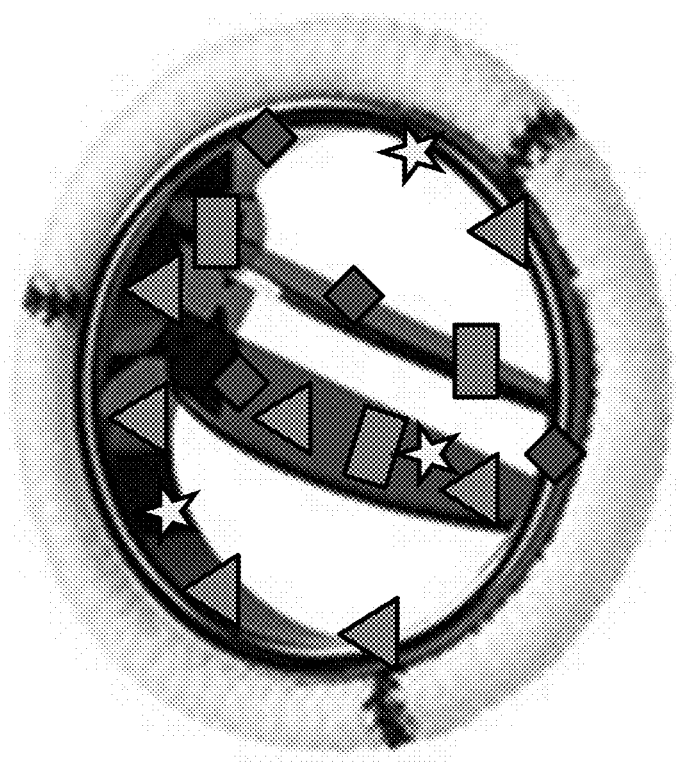
FIG. 6A
FIG. 6B

△ Accelerometer
▢ Contact Sensors
⬢ Position Sensor

△ Accelerometer
▬ Contact Sensors
⬢ Position Sensor

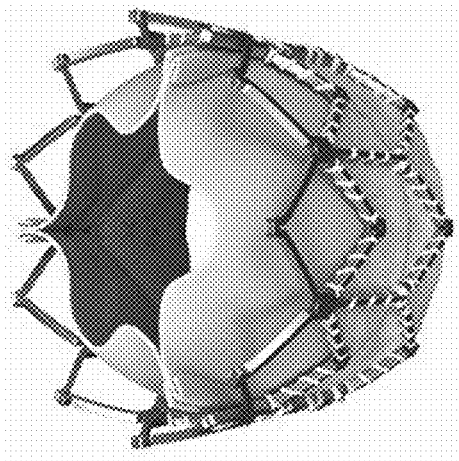
FIG. 12D
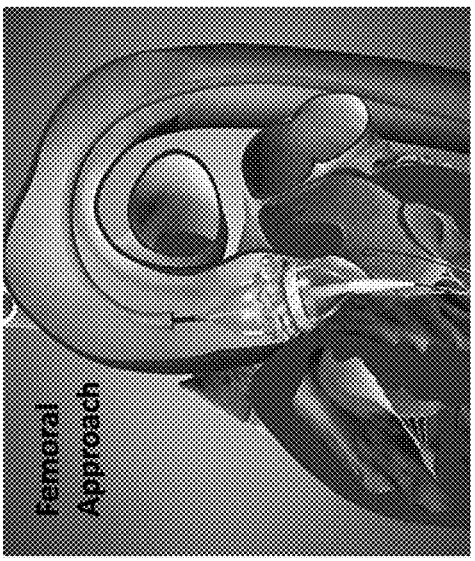
FIG. 12F
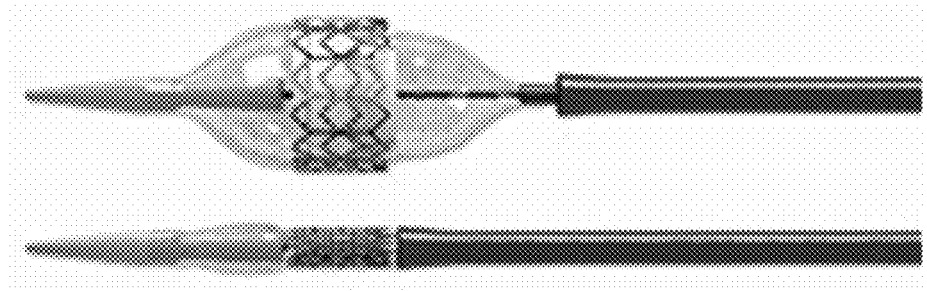
FIG. 12C
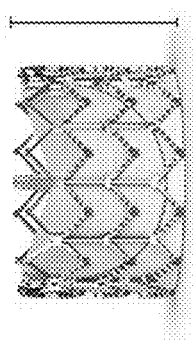
FIG. 12A
FIG. 12B
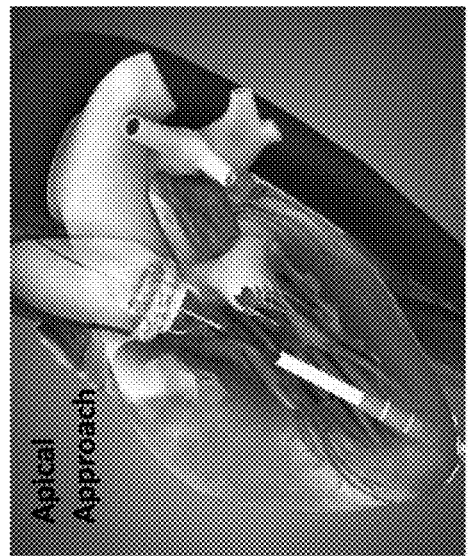
FIG. 12E ◁ Blood /Pressure Sensor
▭ Blood Volume Detectors
◆ Blood Flow Sensor
☆ Metabolic Sensors (pH, glucose, oxygen content, Cholesterol, etc.)

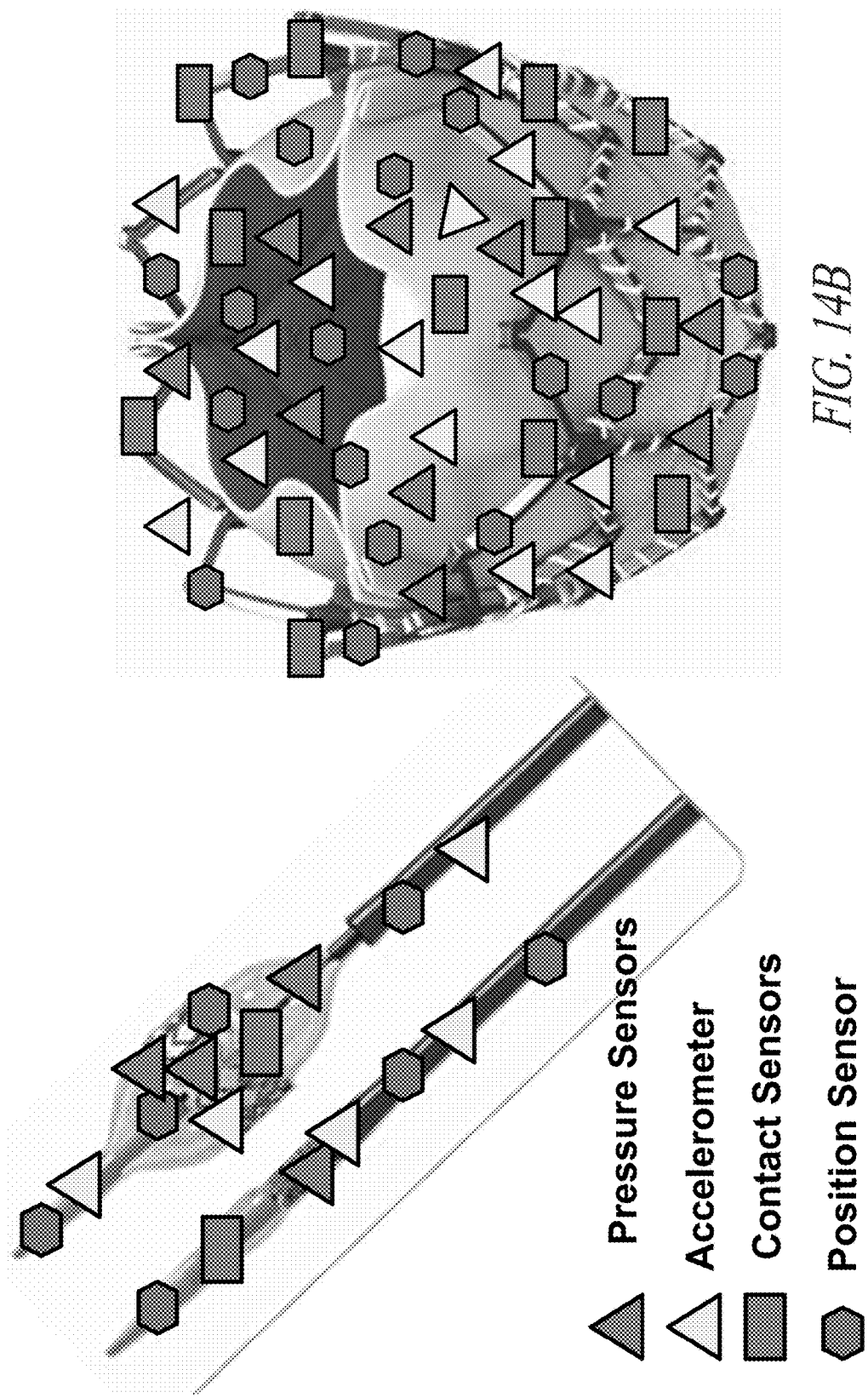

DEVICES, SYSTEMS AND METHODS FOR USING AND MONITORING HEART VALVES

CROSS-REFERENCE TO RELATED APPLICATION

This application is a continuation of U.S. patent application Ser. No. 15/320,296, filed Dec. 19, 2016, which is a national phase application under 35 U.S.C. § 371 of International Application No. PCT/US2015/037810, filed Jun. 25, 2015, which application claims the benefit under 35 U.S.C. § 119(e) of U.S. Provisional Patent Application No. 62/017,161, filed Jun. 25, 2014, which all applications are incorporated herein by reference in their entirety for all purposes.

FIELD OF THE INVENTION

The present invention relates generally to heart valves, and more specifically, to devices and methods for monitoring the placement, efficacy, and performance of a wide variety of heart valves.

BACKGROUND

The heart is the central pump of the body. In humans, the heart is composed of 4 principle chambers: 1) the right atrium, which receives blood from the veins and pumps it into the right ventricle through the tricuspid valve; 2) the right ventricle which receives blood from the right atrium and pumps it through the pulmonary valve into the lungs, where it becomes oxygenated; 3) the left atrium which receives oxygenated blood and pumps it to the left ventricle through the mitral (bicuspid) valve; and 4) the left ventricle which pumps oxygen-rich blood to the rest of the body through the aortic valve.

The heart valves (see FIG. 2) are flaps of tissue (leaflets) that open and close, thereby ensuring that blood flows in one direction. However, heart valves can have congenital complications from birth (e.g., due to stenosis or thickening of the valve; due to misshapen or malformed leaflets; or due to atresia—or failure of the valve orifice to develop), or from disease or trauma that narrows or obstructs flow through the valve (e.g., due to stenosis, calcification, infection, or disease). An additional form of valvular heart disease occurs when valves do not close properly (or incompletely) leading to the backflow of blood into the chamber from which the blood was originally pumped (a process referred to as regurgitation, insufficiency, or prolapse). Mitral valve regurgitation has a prevalence of about 2% of the population, and is one of the two most common valve diseases in the elderly.

Repair of damaged and ineffective heart valves is typically accomplished by replacing the defective native valve with replacement valves, utilizing either tissue-based (biological) valves (which are mostly commonly obtained from pigs) and mechanical or artificial heart valves. While these valves have revolutionized surgical procedures and patient outcomes, they are still subject to a large number of complications.

For example, mechanical heart valve can suffer problems of wear and durability, blockage (from clot, infectious "vegetations"), can cause cavitation (formation of microbubbles), result in red blood cell damage, require the patient to be on anticoagulation therapy for life, and be prone to infection. Tissue-based valves can similarly wear or fatigue over time, become blocked (fibrous tissue, calcifications, clot, vegetations), and/or become infected.

The present invention discloses novel heart valves, as well as related delivery devices which overcome many of the difficulties of previous heart valve-like devices, methods for constructing and monitoring these novel devices, and further provides other related advantages.

SUMMARY

Briefly stated, heart valves having sensors, as well as related delivery devices are provided with a number of sensors to monitor the integrity and efficaciousness of the device.

Within one embodiment, sensors can be positioned within the heart valve, and/or on one or more surfaces of the heart valve. When the phrase "placed in a heart valve" is utilized, it should be understood to refer to any of the above embodiments, unless the context of the usage implies otherwise. Within certain embodiments, the sensors are of the type that are passive and thus do not require their own power supply.

A wide variety of sensors can be utilized within the present invention, including for example, fluid pressure sensors, contact sensors, position sensors, accelerometers, vibration sensors, pulse pressure sensors, liquid (e.g., blood) volume sensors, liquid (e.g., blood) flow sensors, liquid (e.g., blood) chemistry sensors, liquid (e.g., blood) metabolic sensors, mechanical stress sensors, and temperature sensors. Within one embodiment the sensor can be connected with other medical devices that can be utilized to delivery one or more drugs. Within other embodiments the one or more sensors can be a wireless sensor, and/or a sensor that is connected to a wireless microprocessor.

Within particularly preferred embodiments, a plurality of sensors are positioned on the heart valve, and within yet other embodiments more than one type of sensor is positioned on the device. Within other related embodiments the plurality of sensors are positioned on or within the device at a density of greater than 1, 2, 3, 4, 5, 6, 7, 8, 9, 10 or 20 sensors per square centimeter. Within other embodiments the plurality of sensors are positioned on or within the device at a density of greater than 1, 2, 3, 4, 5, 6, 7, 8, 9. 10 or 20 sensors per cubic centimeter. Within either of these embodiments there can be less than 50, 75, 100, or 200 sensors per square centimeter, or per cubic centimeter.

Within other embodiments of the invention each assembly has a unique device identification number. Within further embodiments one or more (or each) of the sensors have a unique sensor identification number. Within yet other embodiments, one or more (or each) of the sensors is uniquely defined within a specific position on or within the device.

According to various embodiments, sensors are placed at different locations in a heart valve in order to monitor the operation, movement, medical imaging (both of the heart valve and associated delivery device, if any, and the surrounding tissues), function, wear, performance, potential side effects, medical status of the patient and the medical status of the heart valve and its interface with the live tissue of the patient. Live, continuous, in situ, monitoring of patient activity, patient function, cardiac function, device activity, device function, performance, placement, surface characteristics (flow and chemical content of fluids moving over or through a surface of the device); presence of inflammatory tissues, bacteria or biofilm on the surface etc.), device forces and mechanical stresses, device and surrounding tissue anatomy (imaging), mechanical and physical integrity of the heart valve, and potential side effects is provided. In addition, information is available on many aspects of the device and its interaction with the patient's own body tissues, including clinically important measurements not currently available through physical examination, medical imaging and diagnostic medical studies.

According to one embodiment, the sensors provide evaluation data of any motion, movement and/or migration of the heart valve during and after placement. Motion sensors and accelerometers can be used to accurately determine the movement of the medical device during physical examination and during normal daily activities between visits. Motion sensors and accelerometers can be used to accurately determine the movement valve leaflets (discs or balls) in situ in order to determine function, degree of closing and the potential for regurgitation. Motion sensors and accelerometers can also be used to accurately determine the movement of the heart valve during placement by the physician.

According to another embodiment, contact sensors are provided between the heart valve and the surrounding tissue and between the moving components (such as leaflets, discs, and balls) of the heart valve. In other embodiments, vibration sensors are provided to detect the vibration between the medical device and the surrounding tissue. In other embodiments, strain gauges are provided to detect the strain between a heart valve and the surrounding tissue. Sudden increases in strain may indicate that too much stress is being placed on the heart valve, which may increase damage to the surrounding body tissues or even result in perforation of the tissues that are being instrumented.

According to other embodiments, accelerometers are provided which detect vibration, shock, tilt and rotation. According to other embodiments, sensors for measuring surface wear, such as contact or pressure sensors, may be embedded at different depths within the heart valve in order to monitor contact of the heart valve with vessel walls, or degradation of the heart valve components over time. In other embodiments, position sensors, as well as other types of sensors, are provided which indicate movement or migration of the medical device in actual use over a period of time.

According to other embodiments, fluid pressure sensors, pulse pressure sensors, liquid (e.g., blood) volume sensors, liquid (e.g., blood) flow sensors, liquid (e.g., blood) chemistry sensors, liquid (e.g., blood) metabolic sensors, contact sensors, and temperature sensors are provided which can monitor the surface environment of the heart valve in situ. Important changes to the surface such as clotting, obstruction, inflammatory tissue (fibrosis), stenosis, infection (bacteria, fungus, pus, white blood cells, biofilm, etc.), narrowing, increased pressure and changes in flow rates through the heart valve can be identified in this manner. Also of great value in the continuous monitoring of patient function, status and health are changes in the content (for example: protein, albumin; white cell counts, red cell counts, PT, PTT, hematocrit, bacteria) and/or chemistry (for example: glucose, calcium, magnesium, electrolytes, phosphate, hemoglobin, ketones, bilirubin, creatinine, blood urea nitrogen, pH, liver enzymes, cardiac enzymes, blood lipids, oxygen levels, therapeutic and illicit drug levels, etc).

According to other embodiments, blood flow rate detectors, blood pressure detectors, and blood volume detectors (e.g., to measure blood volume over a unit of time) located on and within implanted artificial heart valves can measure systolic and diastolic pressure, and estimate systemic vascular resistance and pulmonary vascular resistance. These sensor readings can also be utilized to calculate cardiac output, ejection fraction and cardiac index (key clinical measurements that are valuable in monitoring cardiac-compromised patients, which many valvular patients are).

Within further embodiments, the heart valve can contain sensors at specified densities in specific locations. For example, the heart valve can have a density of sensors of greater than one, two, three, four, five, six, seven, eight, nine, or ten sensors (e.g., accelerometers (acceleration, tilt, vibration, shock and rotation sensors), pressure sensors, contact sensors, flow sensors, position sensors, blood chemistry sensors, blood metabolic sensors, mechanical stress sensors and temperature sensors, or any combination of these) per square centimeter of the device. Within other embodiments, the heart valve can have a density of sensors of greater than one, two, three, four, five, six, seven, eight, nine, or ten sensors [e.g., accelerometers (acceleration, tilt, vibration, shock and rotation sensors)], pressure sensors, flow sensors, contact sensors, position sensors, blood chemistry sensors, blood metabolic sensors, mechanical stress sensors and temperature sensors, or any combination of these) per cubic centimeter of the device.

Within certain embodiments of the invention, the heart valve is provided with a specific unique identifying number, and within further embodiments, each of the sensors on, in or around the heart valve each have either a specific unique identification number, or a group identification number (e.g., an identification number that identifies the sensor as accelerometers (acceleration, tilt, vibration, shock and rotation sensors), pressure sensors, flow, sensors, contact sensors, position sensors, blood chemistry sensors, blood metabolic sensors, mechanical stress sensors and temperature sensors). Within yet further embodiments, the specific unique identification number or group identification number is specifically associated with a position on, in or around the heart valve.

Within other aspects of the invention methods are provided for monitoring an implanted heart valve or device comprising the steps of transmitting a wireless electrical signal from a location outside the body to a location inside the body; receiving the signal at a sensor positioned on, in or around an heart valve or device (and/or delivery device such as a guidewire, catheter or balloon) located inside the body; powering the sensor using the received signal; sensing data at the sensor; and outputting the sensed data from the sensor to a receiving unit located outside of the body.

Within other aspects of the invention methods are provided for imaging a heart valve or device as provided herein, comprising the steps of (a) detecting the location of one or more sensors in a heart valve and/or associated heart valve device (e.g. a delivery device such as a guidewire, catheter or balloon); and (b) visually displaying the location of said one or more sensors, such that an image of the heart valve or delivery device is created. Within various embodiments, the step of detecting may be done over time, and the visual display may thus show positional movement over time. Within certain preferred embodiments the image which is displayed is a three-dimensional image.

The imaging techniques provided herein may be utilized for a wide variety of purposes. For example, within one aspect, the imaging techniques may be utilized during an open surgical procedure or a percutaneous implantation procedure in order to ensure proper placement and working of the heart valve. Within other embodiments, the imaging techniques may be utilized post-operatively in order to examine the heart valve, and/or to compare operation and/or movement (migration) of the device over time.

The integrity of the heart valve can be wirelessly interrogated and the results reported on a regular basis. This permits the health of the patient to be checked on a regular basis or at any time as desired by the patient and/or physician. Furthermore, the heart can be wirelessly interrogated when signaled by the patient to do so (via an external signaling/triggering device) as part of "event recording"—i.e. when the patient experiences a particular event (e.g. chest pain, shortness of breath, syncope, etc.) she/he signals/triggers the device to obtain a simultaneous reading in order to allow the comparison of subjective/symptomatic data to objective/sensor data. Matching event recording data with sensor data can be used as part of an effort to better understand the underlying cause or specific triggers of a patient's particular symptoms. Hence, within various embodiments of the invention methods are provided for detecting and/or recording an event in a subject with one of the heart valve and/or delivery devices provided herein, comprising the interrogating at a desired point in time. Within one aspect of the invention, methods are provided for detecting and/or recording an event in a subject with a heart valve and/or delivery device as provided herein, comprising the step of interrogating at a desired point in time the activity of one or more sensors within the heart valve and/or delivery device, and recording said activity. Within various embodiments, they may be accomplished by the subject and/or by a health care professional (during and after implantation). Within related embodiments, the step of recording may be performed with one or more wired devices, or, wireless devices that can be carried, or worn (e.g., a cellphone, watch or wristband, and/or glasses).

Within further embodiments, each of the sensors contains a signal-receiving circuit and a signal output circuit. The signal-receiving circuit receives an interrogation signal that includes both power and data collection request components. Using the power from the interrogation signal, the sensor powers up the parts of the circuitry needed to conduct the sensing, carries out the sensing, and then outputs the data to the interrogation module. The interrogation module acts under control of a control unit which contains the appropriate I/O circuitry, memory, a controller in the form of a microprocessor, and other circuitry in order to drive the interrogation module. Within yet other embodiments the sensor [e.g., accelerometers (acceleration, tilt, vibration, shock and rotation sensors), pressure sensors, flow sensors, contact sensors, position sensors, blood chemistry sensors, blood metabolic sensors, mechanical stress sensors and temperature sensors) are constructed such that they may readily be incorporated into or otherwise mechanically attached to the heart valve or device (e.g., by way of a an opening or other appendage that provides permanent attachment of the sensor to the heart valve) and/or readily incorporated into body of the heart valve or delivery device.

Within yet other aspects of the invention, methods and devices are provided suitable for transmitting a wireless electrical signal from a location outside the body to a location inside the body; receiving the signal at one of the aforementioned sensors positioned on, in or around a heart valve located inside the body; powering the sensor using the received signal; sensing data at the sensor; and outputting the sensed data from the sensor to a receiving unit located outside of the body. Within certain embodiments the receiving unit can provide an analysis of the signal provided by the sensor.

The data collected by the sensors can be stored in a memory located within the heart valve, or on an associated device (e.g., an external device such as a cellphone, watch, wristband, and/or glasses. During a visit to the physician, the data can be downloaded via a wireless sensor, and the doctor is able to obtain data representative of real-time performance of the heart valve and any associated medical device.

The advantages obtained include more accurate monitoring of the heart valve or device and permitting medical reporting of accurate, in situ, data that will contribute to the health of the patient. The details of one or more embodiments are set forth in the description below. Other features, objects and advantages will be apparent from the description, the drawings, and the claims. In addition, the disclosures of all patents and patent applications referenced herein are incorporated by reference in their entirety.

BRIEF DESCRIPTION OF THE DRAWINGS

FIG. 3A illustrates one example with a restraining cage, occluder ball, and a suture ring. FIG. 3B illustrates a Starr-Edwards valve. FIG. 3C illustrates another version of a Starr-Edwards valve. FIG. 3D illustrates a Smeloff-Cutter valve.

FIG. 5A illustrates a representative bileaflet valve, and depicts the 2 leaflets, leaflet hinges, and the suture ring. FIG. 5B illustrates how blood flows through a trileaflet mechanical valve. FIGS. 5C and 5D illustrate modelling of the valve, and illustrate how a trileaflet mechanical valve opens.

FIG. 6A illustrates a representative bileaflet mechanical valve with sensors. FIG. 6B illustrates a tilting disc mechanical valve with sensors.

FIG. 10A illustrates sensors on the expanded (stent) scaffold, FIG. 10B illustrates sensors on the valvular cusps in the closed position, and FIG. 10C illustrates sensors on both the stent scaffold and the valvular components.

FIGS. 12A, 12B, 12C, 12D, 12E, and 12F illustrate several embodiments of a balloon-expandable percutaneous heart artificial valve, including: FIGS. 12A and 12B, a diagrammatic illustration of a balloon-expandable percutaneous heart valve; FIG. 12C illustrates expansion of a percutaneous heart valve on a balloon catheter delivery device; FIG. 12D illustrates an expanded SAPIEN XT heart valve from Edwards Lifesciences; FIG. 12E (delivery of the device via the apex of the heart—through the chest wall) and 12F (delivery of the device via the vasculature—advancing the catheter into the aorta) illustrate two different delivery approaches for a balloon-expandable percutaneous heart valve.

FIG. 14A illustrates a variety of sensors on a balloon delivery device for a balloon-expandable percutaneous heart valve, as well as a variety of sensors on the balloon itself. FIG. 14B illustrates a variety of sensors on a balloon-expandable percutaneous heart valve.

DETAILED DESCRIPTION OF THE INVENTION

Figure 1:
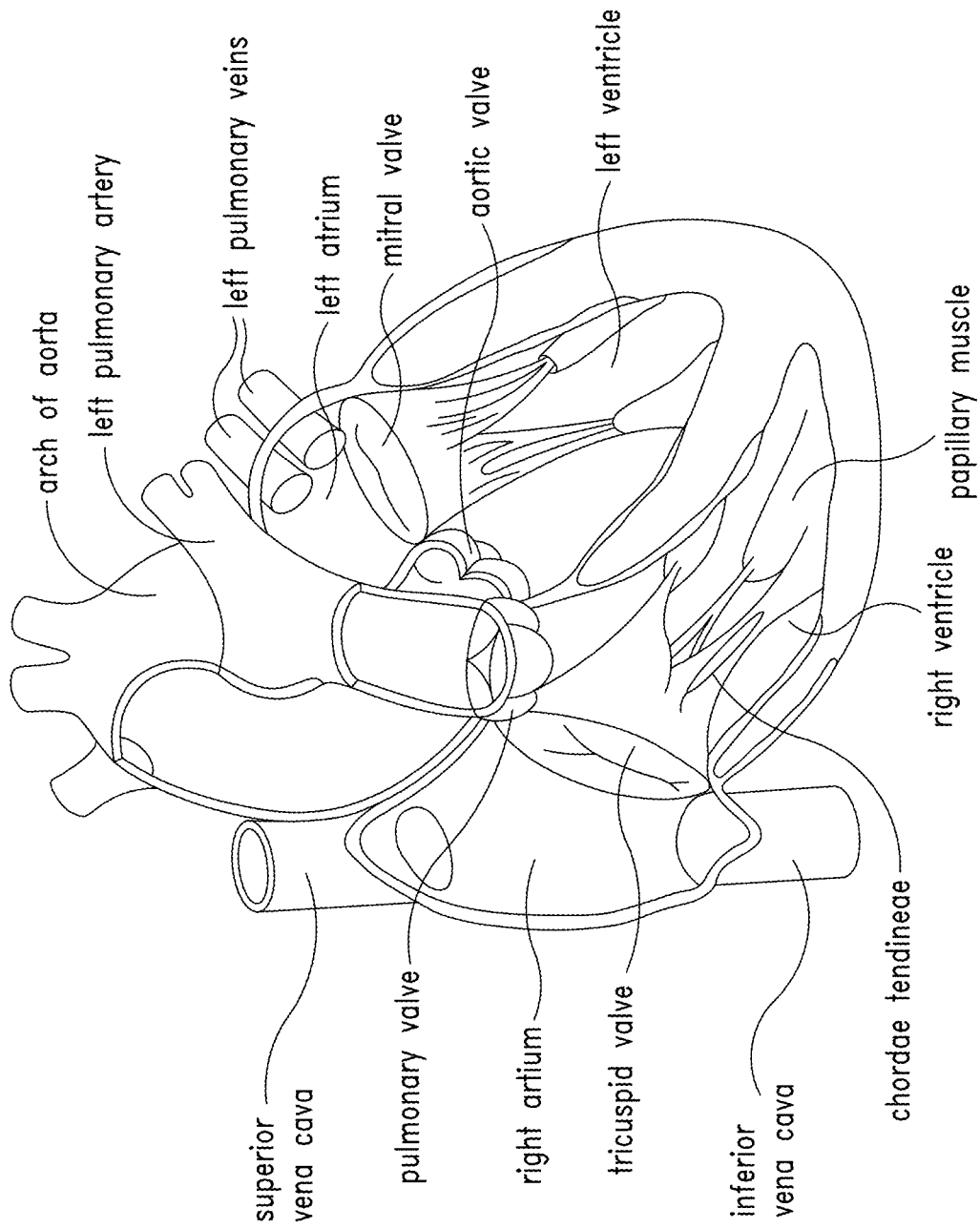
FIG. 1 illustrates a normal heart as well as the location of various anatomical structures including the 4 heart valves.
Figure 2:
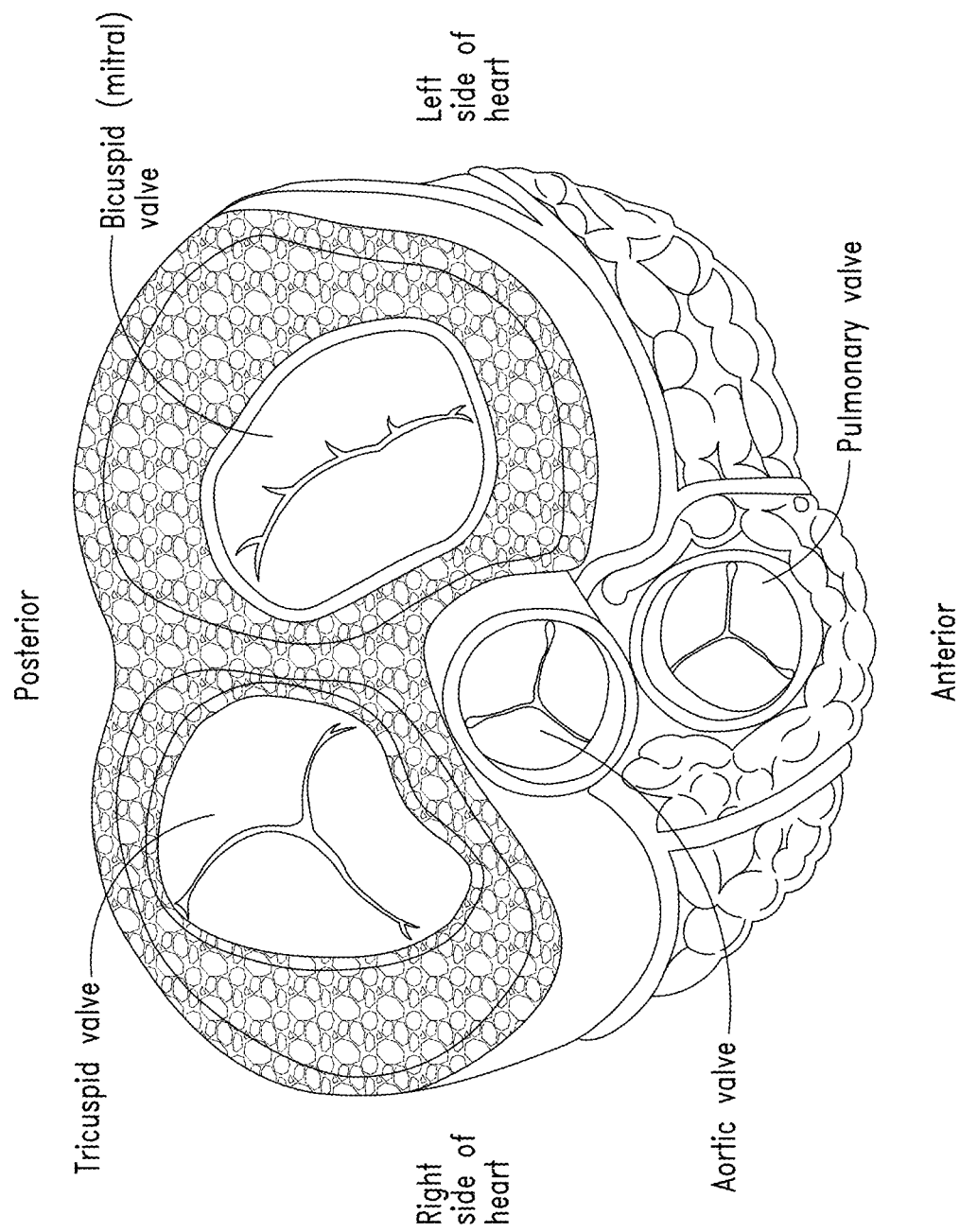
FIG. 2 illustrates the valves of a normal heart depicted in their closed position.

Briefly stated the present invention provides a variety of heart valves that can be utilized to monitor the placement, performance, integrity and/or efficaciousness of the artificial heart valve, and any associated medical device (e.g., a delivery device such as a catheter, balloon or guidewire). Prior to setting forth the invention however, it may be helpful to an understanding thereof to first set forth definitions of certain terms that are used hereinafter.

"Heart valve" refers to a device which can be implanted into the heart of a patient with valvular disease. There are three principle types of heart valves: mechanical, biological, and tissue-engineered (although, for purposes of this disclosure tissue-engineered valves will be considered along with other biological valves). Mechanical valves typically fall into two categories: 1) heart valves for surgical procedures utilizing a sternotomy or "open heart" procedure (e.g., 'caged ball', 'tilting disc', bileaflet and trileaflet designs); and 2) heart valves which are percutaneously implanted [e.g., either a stent framed (self-expanding stent or balloon-expandable stent) or non-stent framed design] that can often contain valve cusps which are fabricated from biological sources (bovine or porcine pericardium). Tissue-based or 'biological' valves are typically made from either porcine or bovine sources, and are typically prepared either from the valve of the animal (e.g., a porcine valve), or from tissue of the pericardial sac (e.g., a bovine pericardial valve or a porcine pericardial valve). Tissue-engineered valves are valves that have been artificially created on a scaffold (e.g., through the growth of suitable cells on a tissue scaffold). Tissue-engineered valves have not yet been commercially adopted.

In addition to heart valves, delivery devices are also provided. In the context of percutaneous delivery, particularly preferred delivery devices comprise a guidewire, delivery catheter (see., e.g., FIGS. 9B, 11 and 12C), catheters with a "sheath" that deploy self-expanding devices (see., e.g., FIGS. 9b and 11), catheters with an expandable balloon (see., e.g., FIG. 12C), and anchoring suture devices. Utilizing such devices and methods heart valves can be replaced without the need for open heart surgery.

Representative examples of heart valves and associated delivery devices are described in U.S. Pat. Nos. 6,564,805, 6,730,122, 7,033,090, 7,578,842, 8,142,497, 8,287,591, and 8,568,474; U.S. Publication Nos. 2010/0076548, 2010/0161046, 2010/117471, 2011/0009818, 2011/0190897, 2012/0179243, 2013/0096671, 2013/0166023, 2013/0268066; and PCT Publication Nos. WO 2012/011108, and WO 2013/021374; all of the above of which are incorporated by reference in their entirety.

The present invention provides heart valves and related delivery devices, all of which have sensors as described in further detail below. The heart valve and related delivery devices are preferably sterile, non-pyrogenic, and/or suitable for use and/or implantation into humans. However, within certain embodiments of the invention the heart valve and/or delivery device can be made in a non-sterilized environment (or even customized or "printed" for an individual subject), and sterilized at a later point in time.

"Sensor" refers to a device that can be utilized to measure one or more different aspects of a body, body fluid, and/or of a heart valve and/or associated delivery device. Representative examples of sensors suitable for use within the present invention include, for example, fluid pressure sensors, contact sensors, position sensors, pulse pressure sensors, liquid (e.g., blood) volume sensors, liquid (e.g., blood) flow sensors, chemistry sensors (e.g., for blood and/or other fluids), metabolic sensors (e.g., for blood and/or other fluids), accelerometers, mechanical stress sensors and temperature sensors. Within certain embodiments the sensor can be a wireless sensor, or, within other embodiments, a sensor connected to a wireless microprocessor. Within further embodiments one or more (including all) of the sensors can have a Unique Sensor Identification number ("USI") which specifically identifies the sensor.

A wide variety of sensors (also referred to as Microelectromechanical Systems or "MEMS", or Nanoelectromechanical Systems or "NEMS", and BioMEMS or BioNEMS, see generally https://en.wikipedia.org/wiki/MEMS) can be utilized within the present invention. Representative patents and patent applications include U.S. Pat. Nos. 7,383,071 and 8,634,928, and U.S. Publication Nos. 2010/0285082, and 2013/0215979. Representative publications include "Introduction to BioMEMS" by Albert Foch, CRC Press, 2013; "From MEMS to Bio-MEMS and Bio-NEMS: Manufacturing Techniques and Applications by Marc J. Madou, CRC Press 2011; "Bio-MEMS: Science and Engineering Perspectives, by Simona Badilescu, CRC Press 2011; "Fundamentals of BioMEMS and Medical Microdevices" by Steven S. Saliterman, SPIE-The International Society of Optical Engineering, 2006; "Bio-MEMS: Technologies and Applications", edited by Wanjun Wang and Steven A. Soper, CRC Press, 2012; and "Inertial MEMS: Principles and Practice" by Volker Kempe, Cambridge University Press, 2011; Polla, D. L., et al., "Microdevices in Medicine," Ann. Rev. Biomed. Eng. 2000, 02:551-576; Yun, K. S., et al., "A Surface-Tension Driven Micropump for Low-voltage and Low-Power Operations," *J. Microelectromechanical Sys.*, 11:5, October 2002, 454-461; Yeh, R., et al., "Single Mask, Large Force, and Large Displacement Electrostatic Linear Inchworm Motors," *J. Microelectromechanical Sys.*, 11:4, August 2002, 330-336; and Loh, N. C., et al., "Sub-10 cm$^3$ Interferometric Accelerometer with Nano-g Resolution," *J.*

*Microelectromechanical Sys.,* 11:3, June 2002, 182-187; all of the above of which are incorporated by reference in their entirety.

Within various embodiments of the invention the sensors described herein may be placed at a variety of locations and in a variety of configurations, on the inside of the heart valve and/or delivery device, within the body of the heart valve and/or delivery device, on the outer surface (or surfaces) of the heart valve and/or delivery device, and/or between the heart valve and any delivery device (e.g., a balloon catheter). Within certain embodiments the heart valve and/or delivery device has sensors at a density of greater than 1, 2, 3, 4, 5, 6, 7, 8, 9, 10 or greater than 10 sensors per square centimeter. Within other aspects the heart valve and/or delivery device has sensors at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter. Within various embodiments the at least one or more of the sensors may be placed randomly, or at one or more specific locations within the heart valve, delivery devices, or kit as described herein.

In various embodiments, the sensors may be placed within specific locations and/or randomly throughout the heart valve or delivery devices, associated medical device (e.g., guidewire or delivery instrument) or kit. In addition, the sensors may be placed in specific patterns (e.g., they may be arranged in the pattern of an X, as oval or concentric rings around the heart valve, associated medical device (e.g., guidewire, catheter, balloon catheter, anchoring suture, or delivery instrument) or kit.

REPRESENTATIVE EMBODIMENTS OF HEART VALVES AND MEDICAL USES OF SENSOR CONTAINING HEART VALVES

In order to further understand the various aspects of the invention provided herein, the following sections are provided below: A. Heart valves and their Use; B. Use of Heart valves to Deliver Therapeutic Agent(s); C. Use of Heart valves having Sensors to Measure Flow and Flow Obstruction; D. Methods for Monitoring Infection in Heart valves; E. Further Uses of Sensor-containing Heart valves in Healthcare; F. Generation of Power from Heart valves; G. Medical Imaging and Self-Diagnosis of Assemblies Comprising Heart valves, Predictive Analysis and Predictive Maintenance; H. Methods of Monitoring Assemblies Comprising Heart valves; and I. Collection, Transmission, Analysis, and Distribution of Data from Assemblies Comprising Heart valves.

A. Heart Valves and Their Use

A1. Mechanical Heart Valves and Their Use

Figure 3B:
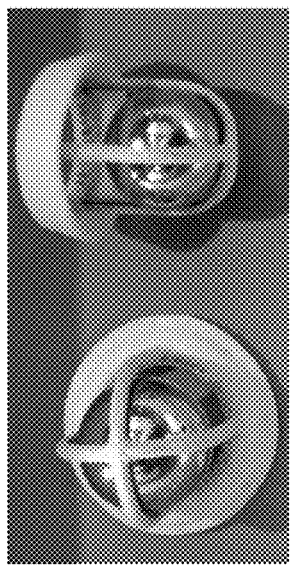
FIGS. 3A, 3B, 3C and 3D illustrate several representative mechanical heart valves based upon a "caged ball" design.
Figure 3C:
Figure 3D:
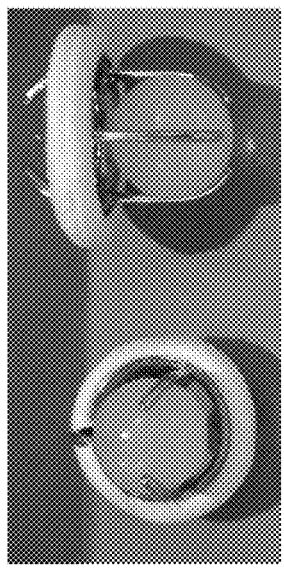
Figure 3A:
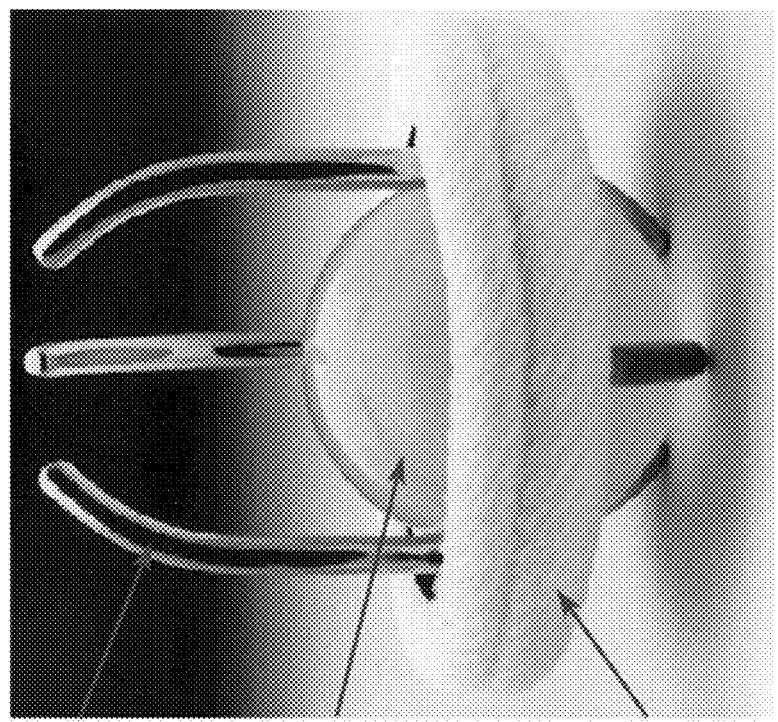
Figure 4:
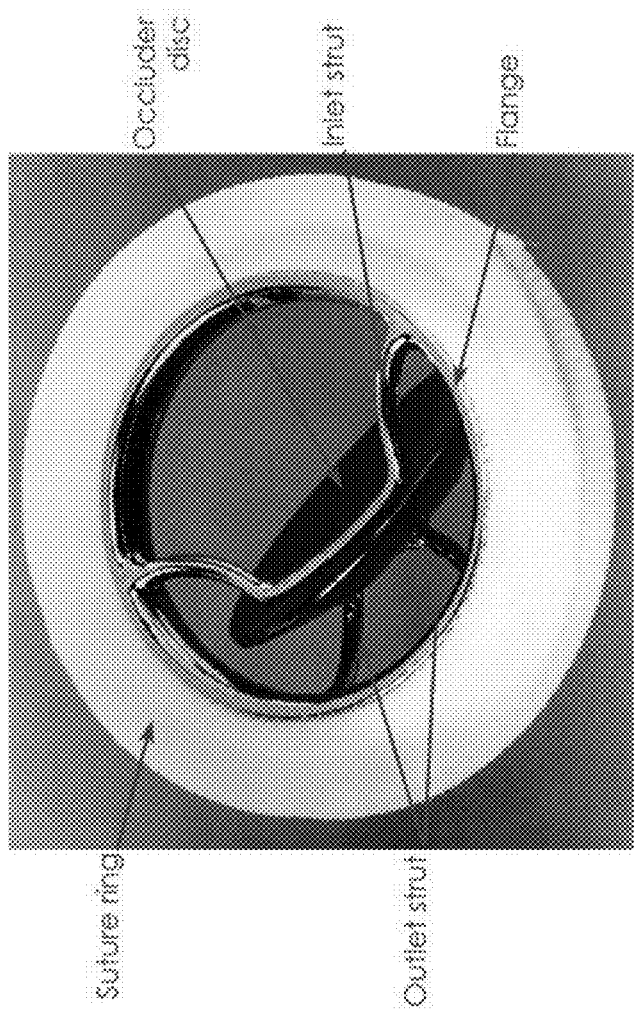
FIG. 4 illustrates a representative 'tilting disc' mechanical valve and depicts the occluding disc and flange, inlet strut and 2 outlet struts, and the suture ring.
Figure 5A:
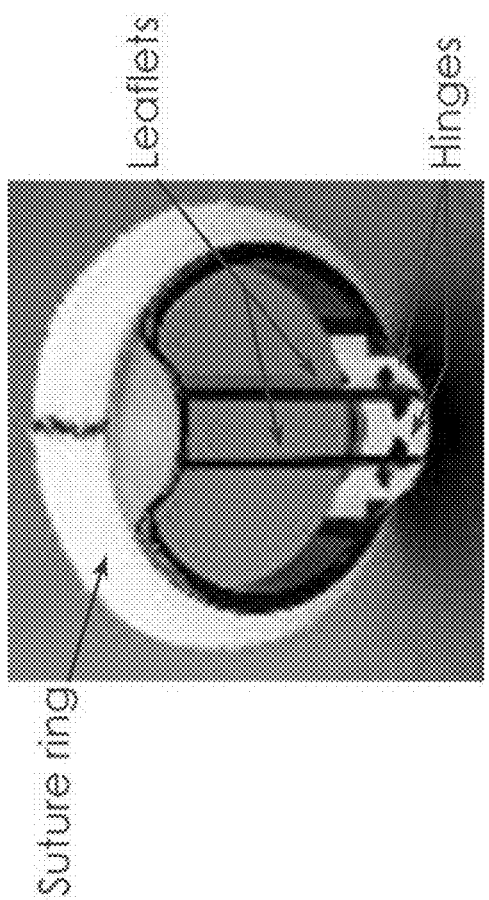
FIGS. 5A, 5B, 5C, and 5D represent several illustrative bileaflet or trileaflet mechanical valves.
Figure 5B:
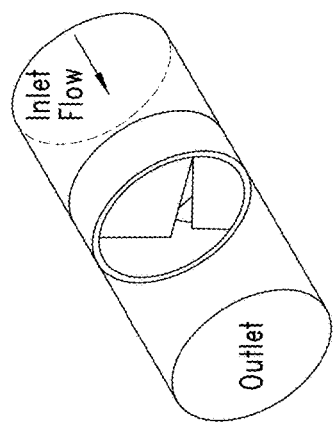
Figure 5C:
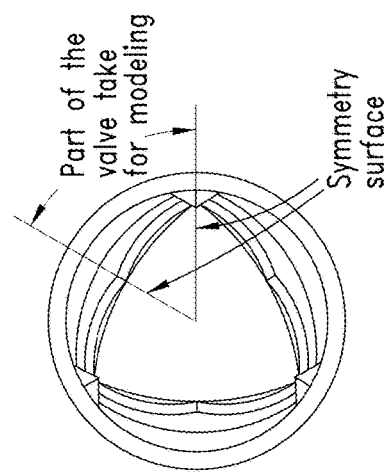
Figure 5D:
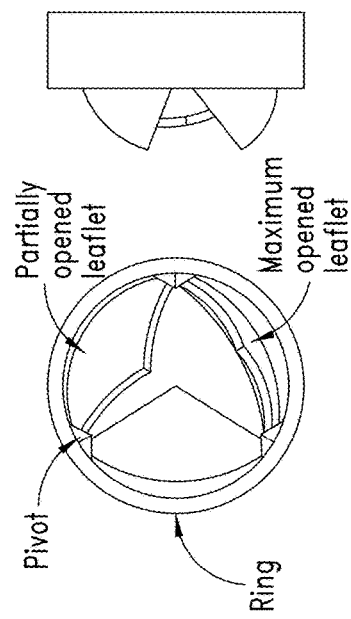
Figure 6D:
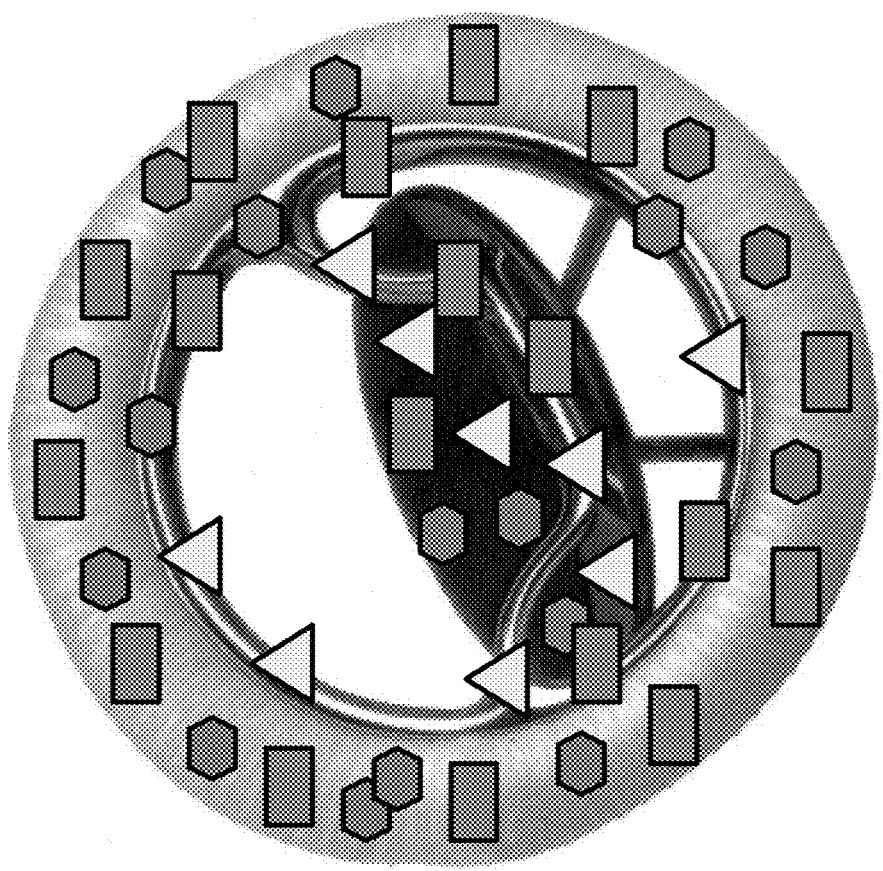
FIG. 6D illustrates a representative tilting disc mechanical valve with sensors.
Figure 6C:
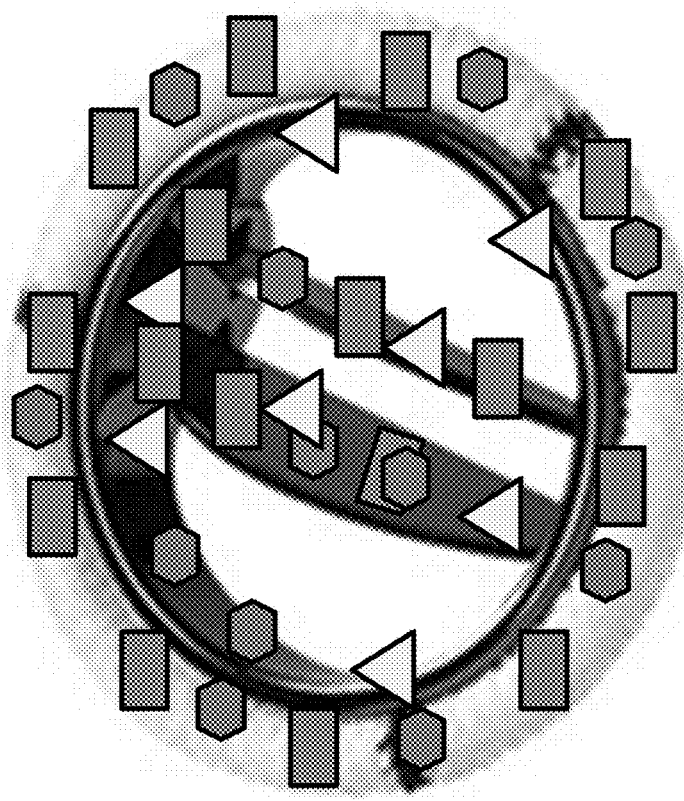
FIG. 6C illustrates a representative bileaflet mechanical valve with sensors.

A1.1 'Open Heart' Surgery Heart Valves: "Caged Ball", "Tilting Disc", and Bi and Tri-Leaflet Designs As noted above, within various embodiments of the invention mechanical heart valves are provided with a variety of the sensors described herein. For example, FIG. 3 illustrates several representative mechanical heart valves based upon a "caged ball" design [e.g., as shown in FIG. 3A such devices have a restraining cage (typically made of metal), an occluder ball (typically made from a silicone elastomer), and a suture ring]. Representative examples include the Starr-Edwards valve as shown in FIGS. 3B and 3C, and the Smeloff-Cutter valve as shown in FIG. 3D. FIG. 4 illustrates a representative "tilting disc" heart valve, showing the various components of the device. Typically there is an occluder disc that rotates on a flange and 2 metal struts (an inlet and an outlet strut) which stop the occluder disc in either the open or the closed position; additionally, there is a metal ring covered by ePTFE that is used as a suture ring to anchor the valve in place. FIG. 5 illustrates several bileaflet or trileaflet valves. FIG. 5A illustrates a representative bileaflet valve, and depicts the two leaflets, leaflet hinges, and the anchoring suture ring. FIG. 5B illustrates how blood flows through a trileaflet valve. FIGS. 5C and 5D illustrate modelling of the valve, as well as illustrating how the leaflets open.

Mechanical valves have improved greatly since their introduction, yet they still suffer from numerous complications. For example, the caged-ball design can last for a long time, but require a lifetime of anticoagulation for the patient. Red blood cells and platelets get damaged flowing through the mechanical valves which can lead to a hypercoagulative state that can result in thrombus and embolis formation (necessitating blood thinner therapy) and can even result in anemia. The leaflet (bileaflet and trileaflet) mechanical valves cause less damage to blood cells (and are less thrombogenic and require lower levels of anticoagulation therapy), but they are vulnerable to backflow, and do not last as long. Mechanical valves are also subject to impact wear (occurs in the hinges of bileaflet valves, between the occluder and ring in tilting disc valves, and between the ball and cage in ball-cage valves) and frictional wear (occurs between the occluder and the struts in tilting disc valves and between the leaflet pivots and hinge cavities in bileaflet valves), and can cause 'cavitation' (i.e., the formation of microbubbles, which can erode the valve surface, increase blood cell damage and increase the incidence of thromboembolic events).

Hence, the present invention provides mechanical heart valves which have one or more sensors, including for example, fluid pressure sensors, contact sensors, accelerometers, vibration sensors, pulse sensors, liquid (e.g., blood) volume sensors, liquid (e.g., blood) flow sensors, liquid (e.g., blood) chemistry sensors, liquid (e.g., blood) metabolic sensors, mechanical stress sensors, and temperature sensors. Such sensors can be placed on, in, or within the various components of the heart valve, and can be utilized to monitor, amongst other things, thrombogenesis, wear, blockage, sticking (impaired movement of the 'valve'), trans-valvular pressure gradients (an indicator of the potential for cavitation), leakage (backflow or regurgitation), detachment of the suture ring (from, for example, suture breakage), assembly of the device (where possible), correct anatomical placement of the device, failure, and safety.

For example, as shown in FIGS. 6A, 6B, 6C and 6D, mechanical valves are illustrated with a variety of sensors. Within one embodiment blood flow (motion) sensors are provided on a mechanical heart valve (e.g., 'caged-ball', 'tilting disc', bi or tri-leaflet valves). The sensors can be provided in specific locations, or diffusively throughout the device. For example, for the tilting disc mechanical valve, sensors can be concentrated on the occluder disc (both sides), as well as on the inlet and outlet struts, flange and suture ring. For the bileaflet (or trileaflet) designs, the sensors can be concentrated on the leaflets (both sides), as well as on the flange and suture ring. For the 'caged-ball' design, the sensors can be concentrated on the ball and cage, as well as on the suture ring.

Blood flow sensors can be utilized to measure fluid flow through the mechanical valve, and to detect abnormalities that occur acutely, or gradually over time. For example, a decrease in forward flow may suggest the development of a stenosis [from thrombus formation, infection (biofilm or vegetations)], sticking of moving components (the ball, disc, or leaflets), or failure of the device. Increases in backwards flow can be suggestive of regurgitation, due to sticking, thrombus, infection or failure of the moving components. Blood flow sensors can show real-time movement of blood through the valve, and permit hemodynamic monitoring and determination of cardiac output (similar to an echocardiogram), ejection fraction and cardiac index (key clinical measurements that are valuable in monitoring cardiac-compromised patients, which many valvular patients are).

Within other embodiments, pressure sensors can be utilized to measure pressure on both sides of the valve, and to detect abnormalities that occur acutely, or gradually over time. For example, an increased pressure gradient can indicate a risk of cavitation. A low pressure gradient can indicate regurgitation and/or possible failure. Pressure sensors on the ventricular side of a valve can measure systolic and diastolic pressure, and estimate systemic vascular resistance and pulmonary vascular resistance (depending upon the valve). These sensor readings can also be utilized to calculate cardiac output, ejection fraction and cardiac index and permit in situ hemodynamic monitoring.

Within further embodiments blood volume sensors can be utilized to measure fluid flow through the valve, and to detect abnormalities that occur acutely, or gradually over time. For example, a decrease in forward blood volume may suggest the development of a stenosis [from thrombus formation, infection (biofilm or vegetations)], sticking of moving components (the ball, disc, or leaflets), or failure of the device. Increases in backwards blood volume (>5 ml) can be suggestive of regurgitation, due to sticking, thrombus, infection or failure of the moving components. Blood volume sensors (e.g., to measure blood volume over a unit of time) can show real-time movement of blood through the valve, and permit hemodynamic monitoring and determination of cardiac output (similar to an echocardiogram), ejection fraction and cardiac index and permit in situ hemodynamic monitoring.

Within yet other embodiments metabolic (or chemical) sensors on mechanical valves can be utilized to measure metabolic parameters important in vascular function. Representative examples include coagulation/clotting parameters such as PT, PTT, clotting time and INR; Blood Oxygen content; Blood $CO_2$ content; Blood pH; Blood cholesterol; Blood lipids (HDL, LDL); Blood Glucose; Cardiac enzymes; Hepatic Enzymes; Electrolytes; Blood Cell Counts; and Kidney Function parameters (BUN, Creatinine, etc.).

Within other embodiments, position sensors are provided that can be utilized to measure the location of fixed and moving components of the mechanical valve. For example, gaps in the leaflets, occlude disc/ring and cage/ball are suggestive of leakage and regurgitation. Position sensors can also be utilized to 'image' valvular motion (opening, closing, and integrity of the seal). Changes in position sensors on the suture ring can show slippage, migration, failure, and suture breakage. Dilation of the ring can indicate possible dilative cardiomyopathy, whereas narrowing of the ring can indicate myocardial hypertrophy.

Within further embodiments contact sensors are provided that can be utilized to measure the contact between fixed and moving components of a mechanical valve. For example, incomplete contact between the leaflets, between the occlude disc and the ring, and between the ball and cage are suggestive of leakage and regurgitation. Contact sensors can also be utilized to 'image' valvular motion (opening, closing, and integrity of the seal). Changes in contact sensors on the suture ring can show slippage, migration, failure, and suture breakage. Contact sensors can also be utilized to monitor the surface of the valve (e.g., to detect the presence of surface anomalies such as the formation of clot or thombi, biofilm or vegetations on the valve surface), and to monitor for friction wear, impact wear, and breakage (e.g., contact sensors can be placed at various depths of any of the various components (e.g., occluder disc, strut, occluder ring, leaflets, leaflet pivots, hinges, ball and/or cage).

Accelerometers can be utilized to measure the location and movement of fixed and moving components of a mechanical valve. For example, gaps in the leaflets, occlude disc and ring, and ball and cage are suggestive of leakage and regurgitation. Accelerometers can also be utilized to 'image' real time valvular motion (opening, closing, and integrity of the seal), and to image changes that might occur in the mechanical valve over time. Changes in accelerometers on the suture ring can show slippage, migration, failure, and suture breakage.

A1.2 Biological (Tissue-Based) Heart Valves and Their Use

Figure 7B:
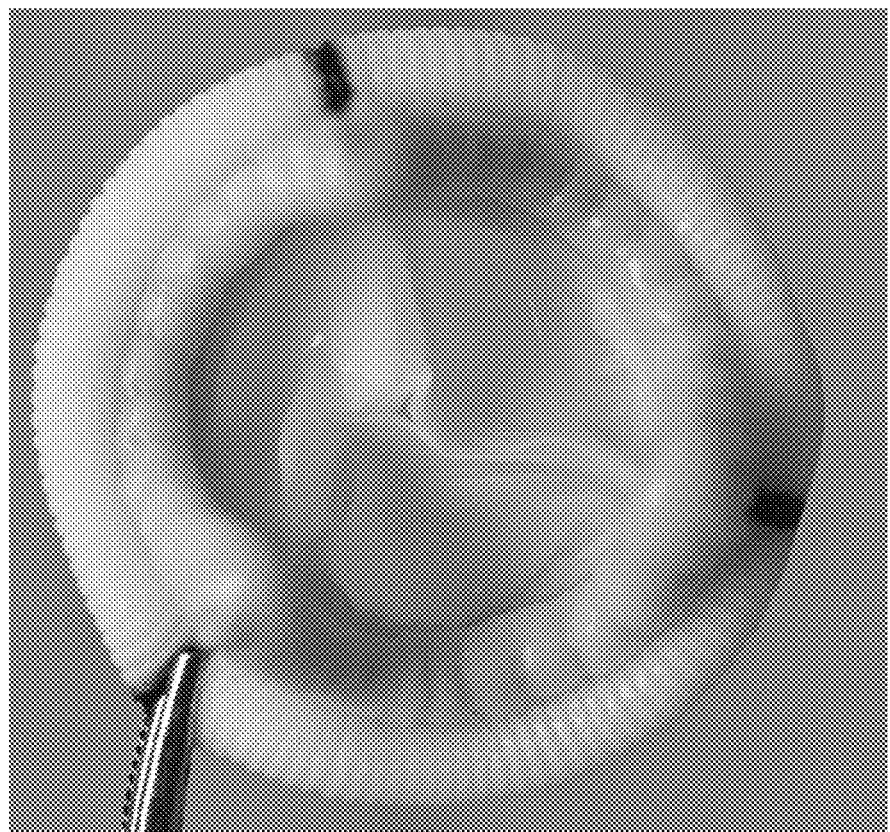
FIG. 7B illustrates a representative tissue (biological) valve made from bovine pericardium.
Figure 7A:
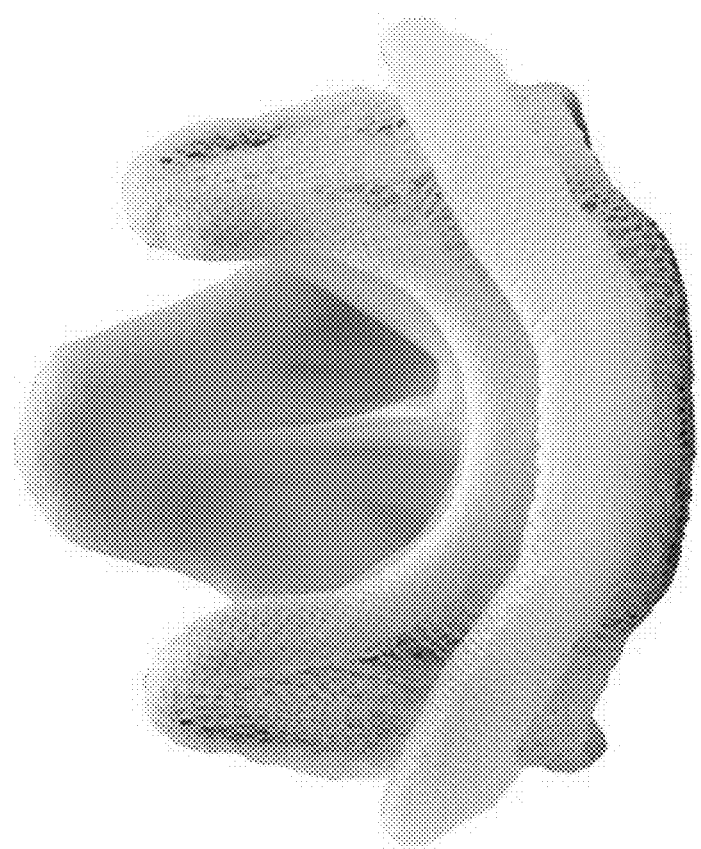
FIG. 7A illustrates a representative tissue (biological) porcine valve.
Figure 8B:
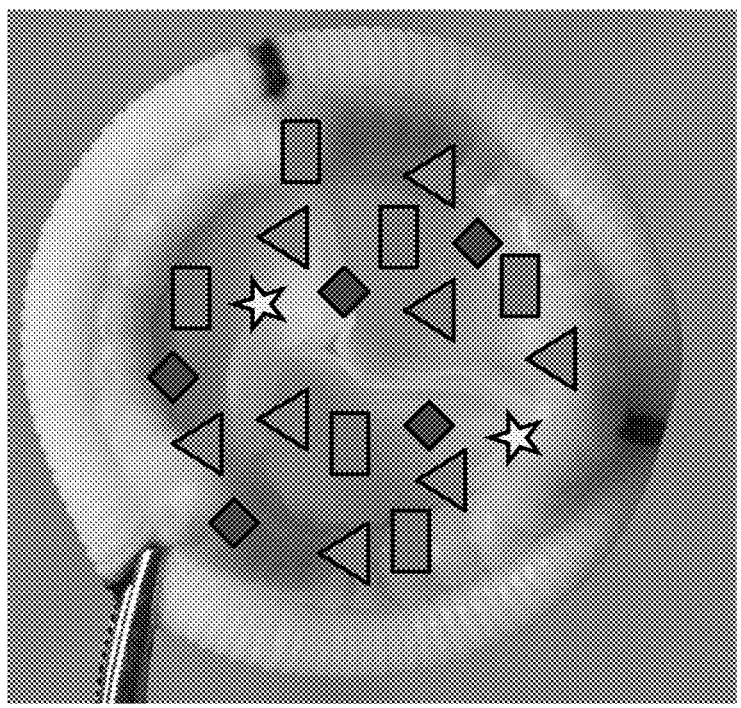
FIG. 8B illustrates a representative bovine valve with a variety of sensors.
Figure 8A:
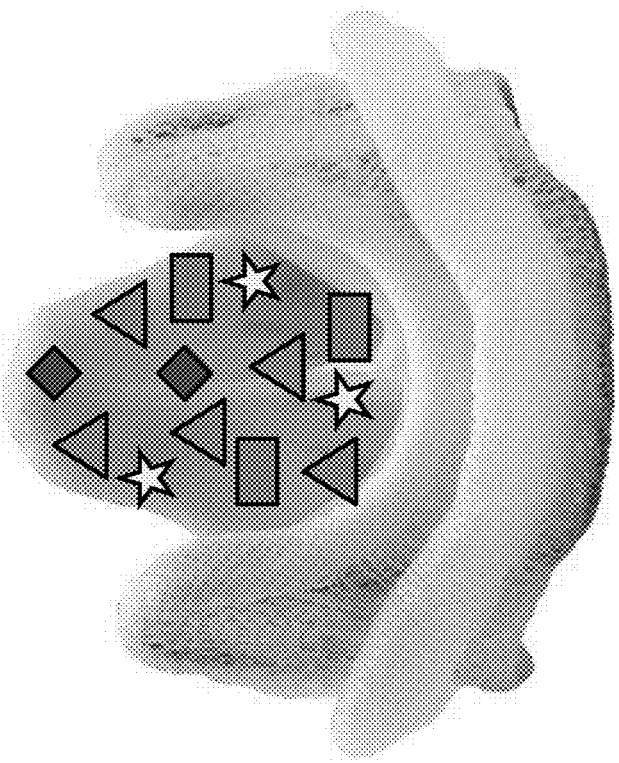
FIG. 8A illustrates a representative porcine valve with a variety of sensors.
Figure 8D:
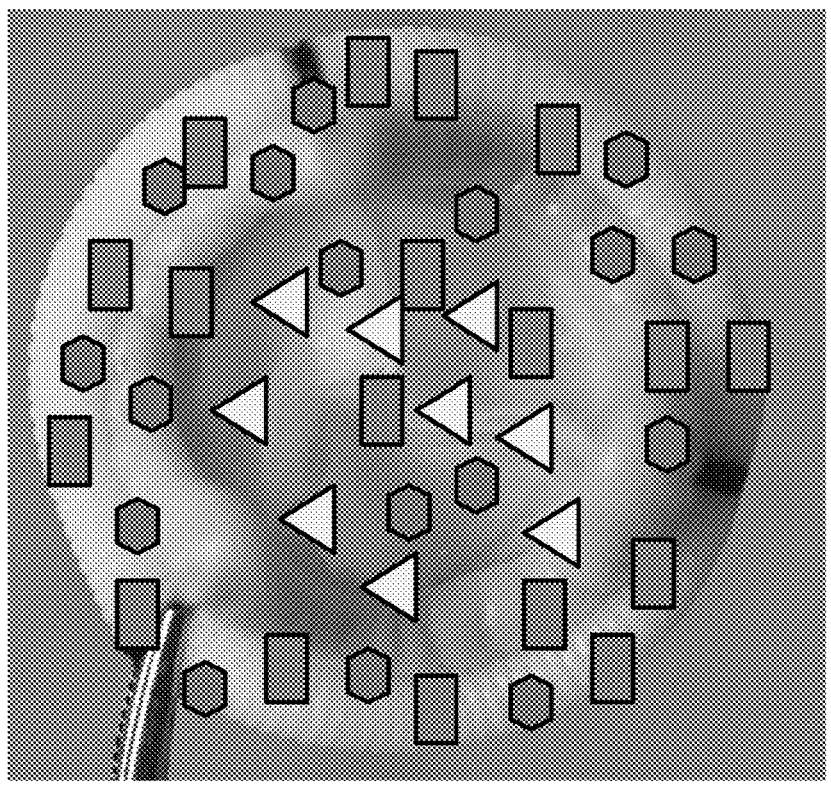
FIG. 8D illustrates a representative bovine valve with a variety of sensors.
Figure 8C:
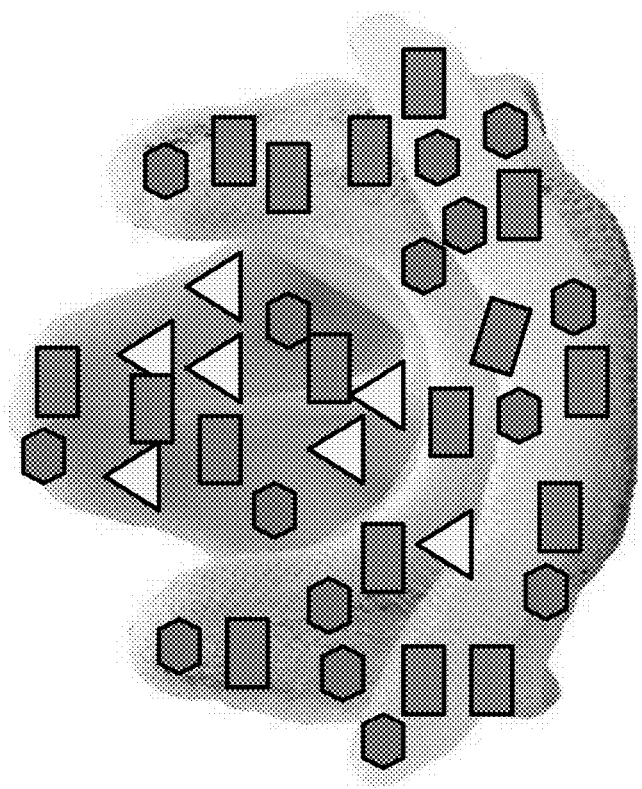
FIG. 8C illustrates a representative porcine valve with a variety of sensors.

As noted above, within various embodiments of the invention biological (tissue-based) heart valves are provided with a variety of sensors described herein. Briefly, biological valves are heart valves that are typically designed from xenographic (i.e., from a different species) tissue. Most typically, biological heart valves are constructed from porcine or bovine (usually either valvular or pericardial) tissue, although other animal tissues (e.g., equine) have also been utilized. Representative examples of biological heart valves are provided in FIG. 7A (an illustration of a porcine valve), and FIG. 7B (an illustration of a valve made from bovine pericardium).

For purposes of this disclosure, tissue-engineered valves can also be considered to be a biological valve. Briefly, tissue-engineered valves generally comprise a layer of cells (e.g., fibroblasts, stem cells, or some combination of cells), that are grown over a tissue scaffold (typically a synthetic polymer-based scaffold, see generally Lichtenberg et al., "Biological scaffolds for heart valve tissue engineering", Methods Mol. Med. 2007; 140:309-17; see also U.S. Pub. No. 2010/117471).

Biological valves have a number of advantages in that they do not damage red blood cells or platelets (and therefore do not require anticoagulation therapy) and they do not cause cavitation to the same degree as mechanical valves. However, they still suffer from several complications, including for example: 1) they have a more limited lifespan than mechanical valves; 2) they can cause an immune reaction; 3) they can clot and form emboli (causing strokes or myocardial infarction); 4) they can also become infected and form septic emboli; 5) they can become covered with fibrous tissue; and 6) they can become calcified. Common biological valves are currently made by Edwards Lifesciences, Medtronic, St. Jude, Sorin, 3F Therapeutics, CryoLife and LifeNet Health.

Hence, the present invention provides biological heart valves which have one or more sensors, including for example, fluid pressure sensors, contact sensors, accelerometers, vibration sensors, pulse sensors, liquid (e.g., blood) volume sensors, liquid (e.g., blood) flow sensors, liquid (e.g., blood) chemistry sensors, liquid (e.g., blood) metabolic sensors, biological stress sensors, and temperature sensors. Such sensors can be place on, in, or within the various components of the heart valve, and can be utilized to monitor, amongst other things, thrombogenesis, infection (vegetations), wear, blockage, sticking (impaired movement of the valve leaflets), trans-valvular pressure gradients, leakage (backflow or regurgitation), detachment of the suture ring (from, for example, suture breakage), correct anatomical placement of the device, failure, and safety.

FIGS. 8A, 8B, 8C, and 8D schematically illustrate biological valves with a variety of sensors. Within one embodiment blood flow (motion) sensors are provided on a biological heart valve. The sensors can be provided in specific locations, or diffusively throughout the device. For example, sensors can be concentrated in, on, and/or within the leaflets, the blood contacting surfaces, and the suture ring.

Blood flow sensors can be utilized to measure fluid flow through the valve, and to detect abnormalities that occur acutely, or gradually over time. For example, a decrease in forward flow may suggest the development of a stenosis [from thrombus formation, infection (biofilm or vegetations), fibrosis, or calcification], sticking of the leaflets, or failure of the device. Increases in backwards flow can be suggestive of regurgitation, due to sticking, thrombus, infection, fibrosis, calcification or failure of the moving components. Blood flow sensors can show real-time movement of blood through the valve, and permit hemodynamic monitoring and determination of cardiac output (similar to an echocardiogram), ejection fraction and cardiac index (key clinical measurements that are valuable in monitoring cardiac-compromised patients, which many valvular patients are).

Within other embodiments, pressure sensors can be utilized to measure pressure on both sides of the valve, and to detect abnormalities that occur acutely, or gradually over time. For example, an increased pressure gradient can indicate a risk of cavitation. A low pressure gradient can indicate regurgitation and/or possible failure. Pressure sensors on the ventricular side of a biological valve can measure systolic and diastolic pressure, and estimate systemic vascular resistance and pulmonary vascular resistance (depending upon the valve). These sensor readings can also be utilized to calculate cardiac output, ejection fraction and cardiac index and permit in situ hemodynamic monitoring.

Within further embodiments blood volume sensors can be utilized to measure fluid volume through the valve, and to detect abnormalities that occur acutely, or gradually over time. For example, a decrease in forward blood volume may suggest the development of a stenosis [from thrombus formation, infection (biofilm or vegetations), fibrosis, calcification], sticking of the leaflets, or failure of the device. Increases in backwards blood volume (>5 ml) can be suggestive of regurgitation, due to sticking, thrombus, infection, fibrosis, calcification, or failure of the moving components. Blood volume sensors (e.g., to measure blood volume over a unit of time) can show real-time movement of blood through the valve, and permit hemodynamic monitoring and determination of cardiac output (similar to an echocardiogram), ejection fraction and cardiac index and permit in situ hemodynamic monitoring.

Within yet other embodiments metabolic (or chemical) sensors can be utilized to measure metabolic parameters important in vascular function. Representative examples include: Coagulation/Clotting parameters such as PT, PTT, clotting time and INR; Blood Oxygen content; Blood $CO_2$ content; Blood pH; Blood cholesterol; Blood lipids (HDL, LDL); Blood Glucose; Cardiac enzymes; Hepatic Enzymes; Electrolytes; Blood Cell Counts; and Kidney Function parameters (BUN, Creatinine, etc.).

Within other embodiments position sensors are provided that can be utilized to measure location of fixed and moving components of a biological valve. For example, gaps in the leaflets (upon closing of the valve) are suggestive of leakage and regurgitation. Position sensors can also be utilized to 'image' valvular motion (opening, closing, and integrity of the seal). Changes in position sensors on the suture ring can show slippage, migration, failure, and suture breakage. Dilation of the ring can indicate possible cardiomyopathy, whereas narrowing of the ring can indicate myocardial hypertrophy.

Within further embodiments contact sensors are provided that can be utilized to measure location of fixed and moving components. For example, gaps in the leaflets (upon closing of the valve) are suggestive of leakage and regurgitation. Contact sensors can also be utilized to 'image' valvular motion (opening, closing, and integrity of the valvular seal). Changes in contact sensors on the suture ring can show slippage, migration, failure, and suture breakage. Contact sensors can also be utilized to monitor the surface of the valve (e.g., to detect the presence of surface anomalies such as the formation of clot or thombi, biofilm or vegetations, fibrosis or calcification on the valve surface), and to monitor for friction wear, impact wear, tears and breakage of the leaflets.

Accelerometers can be utilized to measure the location and movement of fixed and moving components of a biological valve. For example, gaps in the leaflets during valve closure are suggestive of leakage and regurgitation. Accelerometers can also be utilized to 'image' valvular motion (opening, closing, and integrity of the seal), and to image changes that might occur over time. Changes in accelerometers on the suture ring can show slippage, migration, failure, and suture breakage.

A1.3 Percutaneous Heart Valves and Their Use

Within other aspects of the invention percutaneous heart valves (and their associated delivery devices are provided with a variety of sensors described herein. Briefly, percutaneous aortic valve replacement (PAVR) or transcatheter aortic valve replacement (TAVR) is the replacement of the aortic valve through blood vessels or other minimally invasive techniques (thus eliminating a need for 'open-heart' surgery). Typically, the heart is accessed through the femoral artery in the leg, apically (through the apex of the heart), through the subclavian arteries, or the aorta. Two companies have currently approved devices for aortic valve replacement: 1) COREVALVE (Medtronic); and 2) SAPIEN (Edwards Lifesciences). Other percutaneous aortic valves, mitral valves and other heart valves are under development.

Figure 9B:
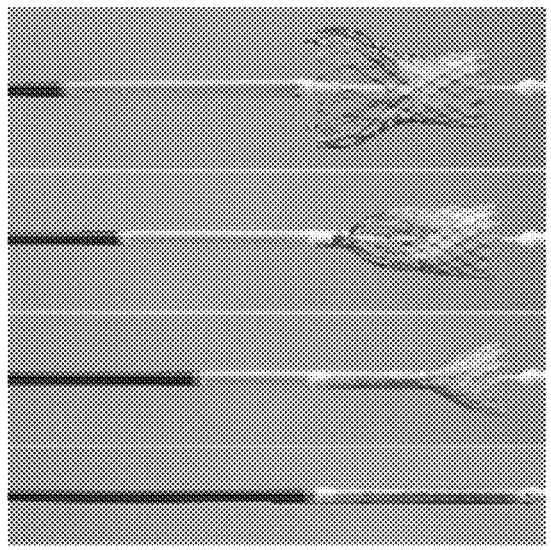
FIGS. 9A, 9B, and 9C illustrate a variety of percutaneous heart valves, including: an expanded scaffold (self-expanding stent) for a heart valve (FIG. 9A); the expansion of a self-expanding percutaneous heart valve (FIG. 9B) as it is released from its delivery catheter; and a percutaneous heart valve being expanded in situ (FIG. 9C) in the aortic valve.
Figure 9C:
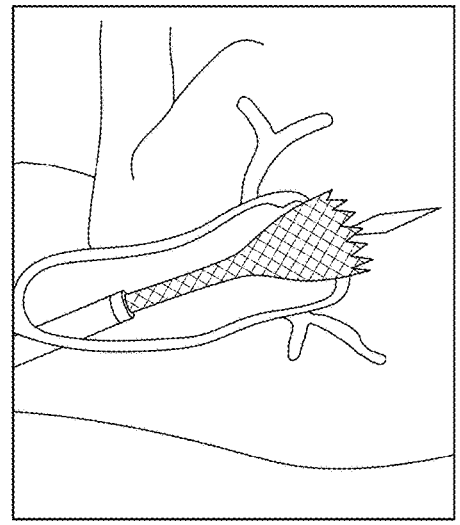
Figure 9A:
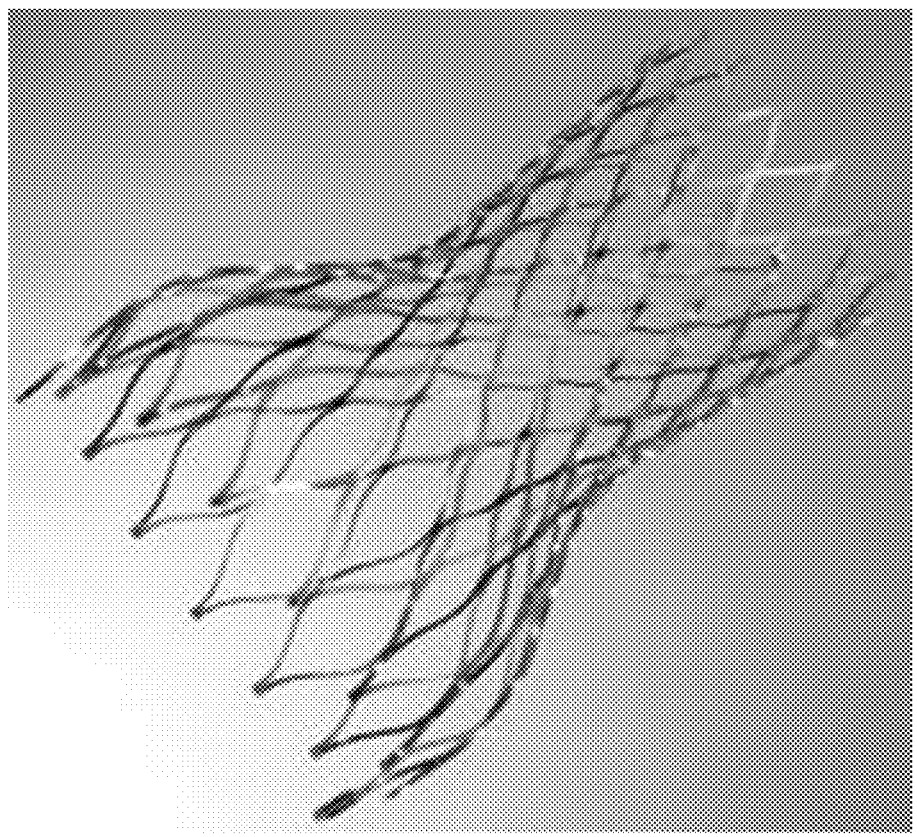
Figure 10B:
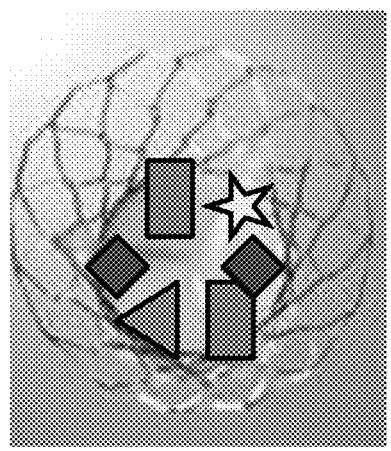
FIGS. 10A, 10B and 10C illustrate a self-expanding percutaneous heart valve with a variety of sensors.
Figure 10C:
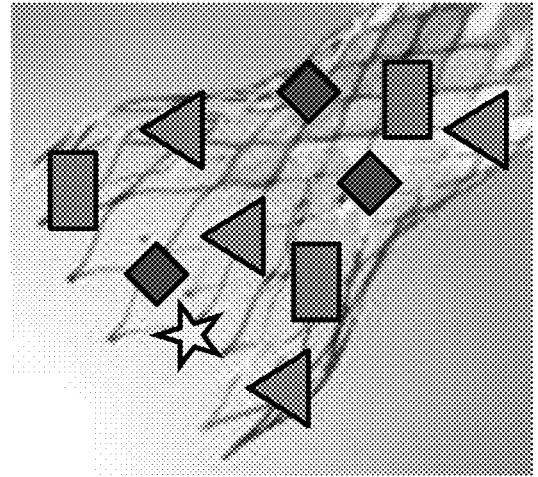
Figure 10A:
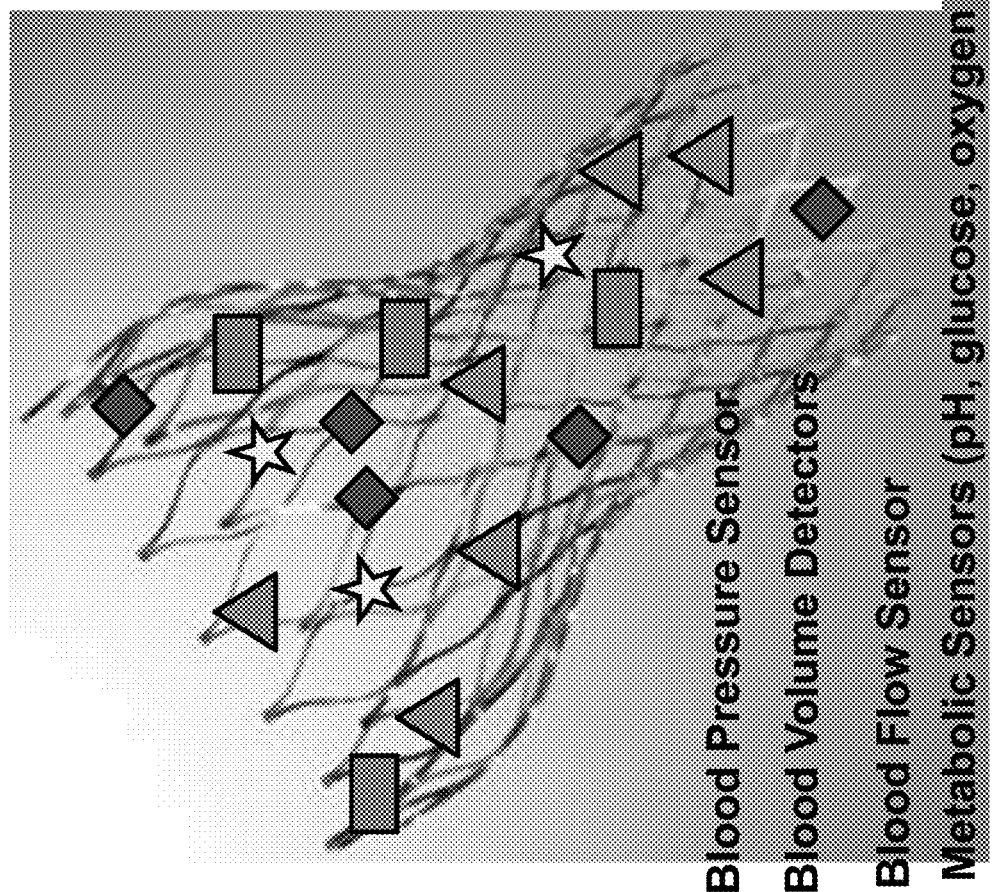

The COREVALVE (Medtronic) is schematically illustrated in FIG. 9. Briefly, it is composed of a self-expanding nitinol support frame (stent) with cells in a diamond design (see FIG. 9A). It is fitted with bovine or procine pericardium shaped into valve leaflets, and provided along with a 18F delivery catheter (see FIGS. 9B and 9C). The SAPIEN (Edwards Lifesciences) is schematically illustrated in FIGS. 12A and B; the SAPIEN XT is depicted in FIG. 12D. It is a trileaflet heart valve constructed of bovine pericardium (see FIG. 12B) which is mounted on a balloon-expandable stainless steel stent (see FIG. 12C).

Percutaneous heart valve delivery has a number advantages, including the fact that they do not require open heart surgery, and hence can be utilized in high-risk patients that might not live through such a surgery. However, they still suffer from complications, including for example: 1) cardiogenic shock, stroke and/or death; 2) perforation of the myocardium; 3) cardiac tamponade; 4) ascending aorta trauma; 5) embolism; 6) thrombosis; 7) valve migration; 8) valve regurgitation; and 9) a variety of other valve dysfunctions (e.g., breaking or fracturing of the valve frame, incomplete expansion, bending, build-up of minerals (calcification) or clots (thrombosis), wear and tear, pannus (fibrous tissue) formation that might block the valve, and failures during the surgical procedure (e.g., to properly size and/or place the valve).

Hence, the present invention provides percutaneous heart valves and/or their associated delivery devices (guidewires, catheters, balloon catheters, anchoring devices) which have one or more sensors, including for example, fluid pressure sensors, contact sensors, position sensors, accelerometers, vibration sensors, pulse sensors, liquid (e.g., blood) volume sensors, liquid (e.g., blood) flow sensors, liquid (e.g., blood) chemistry sensors, liquid (e.g., blood) metabolic sensors, stress sensors, and temperature sensors. Such sensors can be place on, in, or within the various components of the heart valve, and can be utilized to monitor, amongst other things, proper placement of the valve, anatomical location of the valve, pressure exerted on surrounding tissues, balloon inflation/deflation, stent scaffold expansion, deployment of the valve, migration, thrombogenesis, infection (vegetations), calcification, fibrous tissue accumulation, wear, blockage, sticking (impaired movement of the 'valve'), trans-valvular pressure gradients, leakage (backflow or regurgitation), detachment, leaflet damage, assembly of the device (where possible), failure, and safety.

FIGS. 10A, 10B and 10C, 11, 13A, 13B, 13C, 14A and 14B schematically illustrate percutaneous valves and their associated delivery devices (guidewires, catheters, balloon catheters, anchoring devices) with a variety of sensors. Within one embodiment blood flow (motion) sensors are provided on a percutaneous heart valve and/or delivery device. The sensors can be provided in specific locations, or diffusively throughout the valve or delivery device. For example, sensors can be concentrated in, on, and/or within the valve leaflets, the blood contacting surfaces of the valve, and the suture ring. Sensors can also be placed in, on, and/or within the delivery devices.

Blood flow sensors can be utilized to measure fluid flow through the valve and/or delivery device, and to detect abnormalities that occur acutely, or gradually over time. During percutaneous placement of the valve, blood flow sensors on the valve and/or delivery devices can be used to ensure that adequate blood circulation is being maintained and that the device assembly is not critically obstructing cardiac outflow and output. After deployment, changes in flow through the implanted valve can provide valuable clinical information. For example, a decrease in forward flow through the valve leaflets may suggest the development of a stenosis [from thrombus formation, infection (biofilm or vegetations), fibrosis, or calcification], sticking of the leaflets, or failure of the device. Increases in backwards flow can be suggestive of regurgitation, due to sticking, thrombus, infection, fibrosis, calcification or failure of the moving components. Blood flow sensors can also detect leakage through or around the valve frame. Blood flow sensors can show real-time movement of blood through the valve, and permit hemodynamic monitoring and determination of cardiac output (similar to an echocardiogram), ejection fraction and cardiac index (key clinical measurements that are valuable in monitoring cardiac-compromised patients, which many valvular patients are).

Within other embodiments, pressure sensors can be utilized to measure pressure on both sides of the valve and/or delivery device, and to detect abnormalities that occur acutely, or gradually over time. During percutaneous placement of the valve, pressure sensors on the valve (particularly the metallic stent scaffold) and/or delivery devices (particularly the delivery balloon) can be used to monitor the pressure being applied to surrounding tissues. This can help prevent procedural complications such as damage to the wall of the aorta or myocardium and/or perforation of these tissues. After deployment, changes in pressures across the implanted valve can provide valuable clinical information. For example, an increased pressure gradient across the valve can indicate a risk of cavitation. A low, or decreasing, pressure gradient can indicate regurgitation and/or possible valve failure. Pressure sensors on the ventricular and aortic side of a percutaneous valve can measure systolic and diastolic pressure, and estimate systemic vascular resistance. These sensor readings can also be utilized to calculate cardiac output, ejection fraction and cardiac index and permit in situ hemodynamic monitoring.

Within further embodiments blood volume sensors can be utilized to measure fluid flow through the percutaneous valve and/or associated delivery devices, and to detect abnormalities that occur acutely, or gradually over time. During percutaneous placement of the valve, blood volume sensors on the valve and/or delivery devices can be used to ensure that adequate systemic blood volume is being maintained and that the device assembly is not critically obstructing cardiac outflow and output. After deployment, changes in blood volume through the implanted valve can provide valuable clinical information. For example, a decrease in forward blood volume may suggest the development of a stenosis [from thrombus formation, infection (biofilm or vegetations), fibrosis, calcification], sticking of the leaflets, or failure of the device. Increases in backwards blood volume (>5 ml) can be suggestive of regurgitation, due to sticking, thrombus, infection, fibrosis, calcification, or failure of the moving components. Blood volume sensors (e.g., to measure blood volume over a unit of time) can show real-time movement of blood through the valve, and permit hemodynamic monitoring and determination of cardiac output (similar to an echocardiogram), ejection fraction and cardiac index and permit in situ hemodynamic monitoring.

Within yet other embodiments metabolic (or chemical) sensors can be utilized on the valve and/or delivery devices to measure metabolic parameters important in vascular function. Representative examples include Coagulation/Clotting parameters such as PT, PTT, clotting time and INR; Blood Oxygen content; Blood $CO_2$ content; Blood pH; Blood cholesterol; Blood lipids (HDL, LDL); Blood Glucose; Cardiac enzymes; Hepatic Enzymes; Electrolytes; Blood Cell Counts; and Kidney Function parameters (BUN, Creatinine, etc.).

Within other embodiments position sensors are provided that can be utilized on the percutaneous valve and/or associated delivery devices to measure the location of fixed and moving components. During percutaneous placement of the valve, position sensors on the valve and/or delivery devices are invaluable in assisting in correct anatomical placement of the artificial valve across the native valve. Monitoring position changes of the device in "real time" during deployment can help the clinician place and secure the device correctly. After deployment, changes in position of the implanted valve can indicate migration of the device away (upstream or downstream) from its original placement site. Position sensors can also be utilized to monitor valve function after implantation. For example, gaps in the leaflets upon closing of the valve are suggestive of leakage and regurgitation. Position sensors can also be utilized to 'image' valvular leaflet motion (opening, closing, and integrity of the seal). Changes in position sensors located on the stent scaffold can show slippage, migration, failure, and anchoring suture breakage. Dilation of the scaffold can indicate possible overexpansion, breakage or failure; whereas narrowing of the scaffold can indicate possible underexpansion, collapse, breakage, or failure.

Within further embodiments contact sensors are provided that can be utilized on the percutaneous valve and/or associated delivery devices to measure the contact between the device and the surrounding tissues, the contact between related device components/moving pieces, and the status of blood-contacting surface of the device. During percutaneous placement of the valve, contact sensors on the valve and/or delivery devices are invaluable in assisting in correct anatomical placement of the artificial valve across the native valve. Monitoring contact changes of the device in "real time" during deployment can help the clinician place, size, and secure the device correctly. In addition, contact sensors on the valve (particularly the metallic stent scaffold) and/or delivery devices (particularly the delivery balloon) can be used to monitor the amount and extent of contact with surrounding tissues. This can help prevent procedural complications such as damage to the wall of the aorta or myocardium (and/or perforation of these tissues), monitor for correct inflation and full deflation of the balloon catheter (if present), and full deployment of the stent scaffold across the native valve. After deployment, changes in contact between the implanted valve and surrounding tissues can indicate migration of the device away (upstream or downstream) from its original placement site. Contact sensors can also be utilized to monitor valve function after implantation. For example, gaps in the valve leaflets (upon closing) are suggestive of leakage and regurgitation. Contact sensors can also be utilized to 'image' valvular motion (opening, closing, and integrity of the seal) in real time. Increased contact between the stent scaffold and the vascular wall can indicate possible overexpansion, breakage or failure; whereas decreased contact between the stent scaffold and the vascular wall can indicate possible underexpansion, collapse, breakage, or failure. Contact sensors can also be utilized to monitor the blood-contacting surface of the valve (e.g., e.g., to detect the presence of surface anomalies such as the formation of clot or thombi, biofilm or vegetations, fibrosis or calcification on the valve surface), and to monitor for friction wear, impact wear, tears and breakage of the leaflets.

Accelerometers can be utilized to measure the location and movement of fixed and moving components on the valve and/or delivery devices. During percutaneous placement of the valve, accelerometers on the valve and/or delivery devices are invaluable in assisting in correct anatomical placement of the artificial valve across the native valve. Monitoring movement of the device in "real time" during deployment can help the clinician place, size, and secure the device correctly. In addition, accelerometers on the valve (particularly the metallic stent scaffold) and/or delivery devices (particularly the delivery balloon) can be used to monitor the interaction between the device(s) and surrounding tissues. This can help prevent procedural complications such as damage to the wall of the aorta or myocardium (and/or perforation of these tissues), monitor for correct inflation and full deflation of the balloon catheter (if present), and full deployment of the stent scaffold across the native valve. After deployment, movement of the implanted valve can indicate migration of the device away (upstream or downstream) from its original placement site. Accelerometers can also be utilized to monitor valve function after implantation. For example, gaps in the valve leaflets (when in the closed position) are suggestive of leakage and regurgitation. Accelerometers can also be utilized to 'image' valvular motion (opening, closing, and integrity of the seal), and to image changes that might occur over time. Accelerometers can detect changes in the stent scaffold: increases in diameter are indicative of possible overexpansion, breakage or failure; whereas decreases in the diameter can indicate possible underexpansion, collapse, breakage, or failure.

Figure 11:
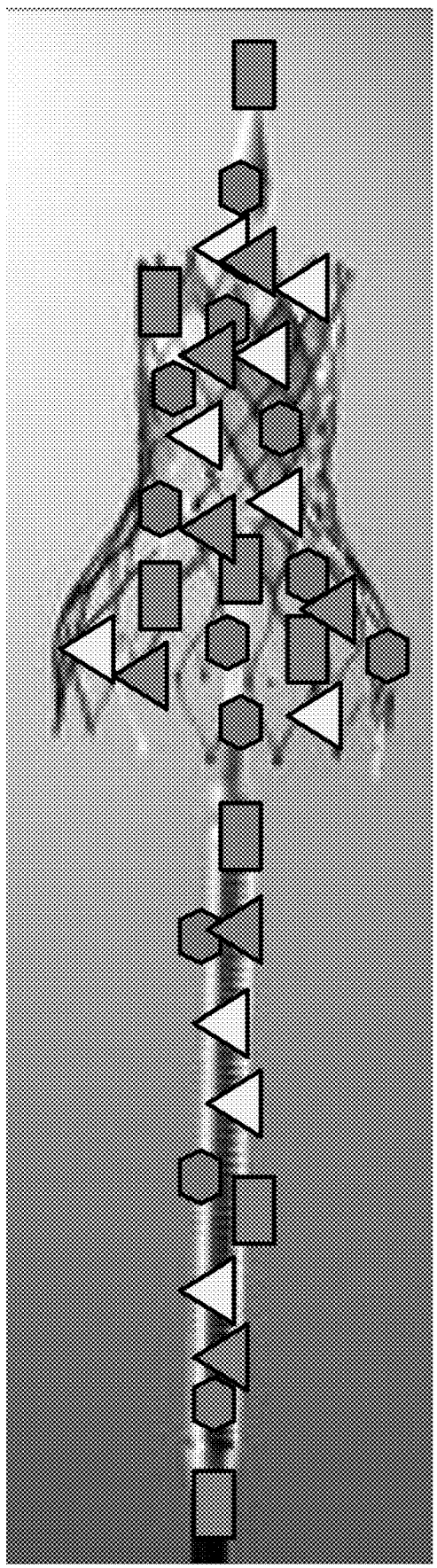
FIG. 11 illustrates a representative percutaneous heart valve with sensors on a representative delivery system with sensors.
Figure 13C:
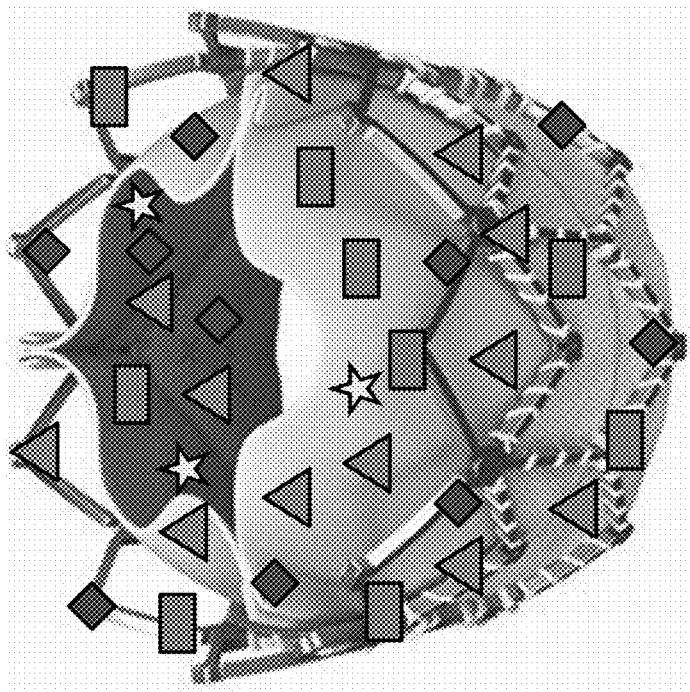
FIGS. 13A (valvular cusps), 13B (supporting stent) and 13C (both valvular cusps and supporting stent) illustrate a variety of sensors on a balloon-expandable percutaneous heart valve.
Figure 13B:
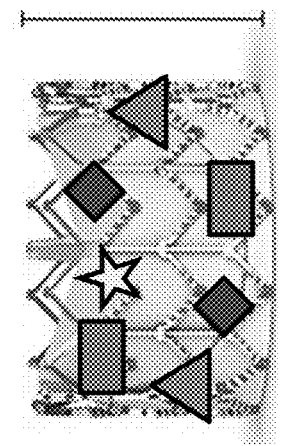
Figure 13A:
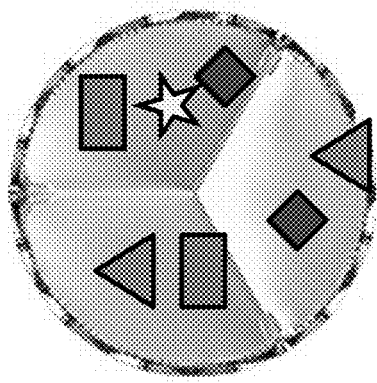

Within further embodiments of the invention sensors are utilized on the heart valve and delivery devices in tandem in order to ensure proper placement and deployment of the heart valve (see FIG. 11 and FIG. 14A). Utilizing for example, position sensors, accelerometers, and/or contact sensors, a physician can help to ensure: 1) accurate placement across the native valve; 2) imaging during placement; 3) full balloon deployment and deflation; 4) full stent (heart valve) deployment and expansion; and 5) movement or migration during or subsequent to the procedure.

A1.4 General Consideration Regarding Heart Valves

Within various embodiments of the invention, methods are also provided for manufacturing a heart valve having one of the sensors provided herein. For example, within one embodiment of the invention a heart valve (e.g., mechanical or biological) is constructed such that one or more sensors provided herein are placed directly into the heart valve at the time of manufacture, and subsequently sterilized in a manner suitable for use in subjects.

In one embodiment, a biological valve may be prepared by customary means (see generally, "Heart Valves: From Design to Clinical Implantation", Iaizzo, Bianco, Hill and St. Louis, eds. Springer, New York, 2015, which is incorporated by reference in its entirety). Sensors provided herein may be directly implanted into the tissue of an artificial biological valve, and subsequently implanted into a patient.

Within further embodiments, scaffolds can be prepared for a heart valve (see, e.g., U.S. Pat. No. 8,562,671, and WO 2013/142879 which are incorporated by reference in their entirety). Briefly, scaffolds composed of one or more compounds (e.g., polymers) can be prepared in order to mimic the shape of a heart valve (or portion thereof). Sensors can be placed into the structure before, during, or subsequent to manufacture of the valve (e.g., in the case or electrospinning or molding of polymer fibers, or in the case of 3D printing as described in more detail below). Within certain preferred embodiments the scaffold can be seed with stem cells suitable for growth of tissue on the artificial heart valve (see, e.g., WO 1999/003973 and U.S. Pat. No. 8,852,571, which are incorporated by reference in their entirety).

Within further embodiments, the present disclosure provides a method of making a heart valve by 3D printing, additive manufacturing, or a similar process whereby the heart valve is formed from powder or filament that is converted to a fluid form such subsequently solidifies as the desired shape. For convenience, such processes will be referred to herein as printing processes or 3D printing processes. The present disclosure provide a method of making a heart valve by a printing process, where that heart valve includes a sensor, circuit or other feature as disclosed herein (collectively sensor or sensors). The sensor may be separately produced and then incorporated into the heart valve during the printing process. For example, a sensor may be placed into a desired position and the printing process is carried out around the sensor so that the sensor becomes embedded in the printed heart valve. Alternatively, the printing process may be started and then at appropriate times, the process is paused to allow a sensor to be placed adjacent to the partially completed heart valve. The printing process is then re-started and construction of the heart valve is completed. The software that directs the printing process may be programmed to pause at appropriate predetermined times to allow a sensor to be added to the partially printed heart valve.

In addition, or alternatively, the sensor itself, or a portion thereof may be printed by the 3D printing process. Likewise, electronic connectively to, or from, or between, sensors may be printed by the 3D printing process. For example, conductive silver inks may be deposited during the printing process to thereby allow conductivity to, or from, or between sensors of a heart valve. See, e.g., PCT publication nos. WO 2014/085170; WO 2013/096664; WO 2011/126706; and WO 2010/0040034 and US publication nos. US 2011/0059234; and US 2010/0037731. Thus, in various embodiments, the present disclosure provides heart valves wherein the sensor is printed onto a substrate, or a substrate is printed and a sensor is embedded or otherwise incorporated into or onto the substrate, or both the substrate and the sensor are printed by a 3D printing technique.

3D printing may be performed using various printing materials, typically delivered to the 3D printer in the form of a filament. Two common printing materials are polylactic acid (PLA) and acrylonitrile-butadiene-styrene (ABS), each being an example of a thermoplastic polymer. When strength and/or temperature resistance is particularly desirable, then polycarbonate (PC) may be used as the printing material. Other polymers may also be used. See, e.g., PCT publication nos. WO 2014/081594 for a disclosure of polyamide printing material. When metal parts are desired, a filament may be prepared from metal or metal alloy, along with a carrier material which ultimately will be washed or burned or otherwise removed from the part after the metal or metal alloy has been delivered.

When the heart valve is of a particularly intricate shape, it may be printed with two materials. The first material is cured (using, e.g., actinic radiation) as it is deposited, while the second material is uncured and can be washed away after the heart valve has been finally printed. In this way, significant hollow spaces may be incorporated into the heart valve.

Additive manufacturing is a term sometimes used to encompass printing techniques wherein metal or metal allow is the material from which the desired part is made. Such additive manufacturing processes utilizes lasers and build an object by adding ultrathin layers of materials one by one. For example, a computer-controlled laser may be used to direct pinpoint beams of energy onto a bed of cobalt-chromium alloy powder, thereby melting the alloy in the desired area and creating a 10-30-micron thick layer. Adjacent layers are sequentially and repetitively produced to create the desired sized item. As needed, a sensor may be embedded into the alloy powder bed, and the laser melts the powder around the sensor so as to incorporate the sensor into the final product. Other alloys, including titanium, aluminum, and nickel-chromium alloys, may also be used in the additive manufacturing process. See, e.g., PCT publication nos. WO 2014/083277; WO 2014/074947; WO 2014/071968; and WO 2014/071135; as well as US publication nos. US 2014/077421; and US 2014/053956.

Accordingly, in one embodiment the present disclosure provides a method of fabricating a sensor-containing heart valve, the method comprising forming at least one of a sensor and a support for the sensor using a 3D printing technique. Optionally, the 3D printing technique may be an additive manufacturing technique. In a related embodiment, the present disclosure provides a heart valve that is produced by a process comprising a 3D printing process, such as an additive manufacturing process, where the heart valve includes a sensor.

Disclosure of 3D printing processes and/or additive manufacturing is found in, for example PCT publication nos. WO 2014/020085; WO 2014/018100; WO 2013/179017; WO 2013/163585; WO 2013/155500; WO 2013/152805; WO 2013/152751; WO 2013/140147 and US publication nos. 2014/048970; 2014/034626; US 2013/337256; 2013/329258; US 2013/270750.

As briefly noted above, heart valves (e.g., mechanical, biological or percutaneous heart valves) and their associated delivery devices (guidewires, catheters, balloon catheters, and anchoring devices if present) of the present invention can have a wide variety and number of sensors. The sensors can be incorporated on the surface of (in or on), or within the heart valve or delivery devices. Representative examples of sensors include contact sensors, strain gauge sensors, pressure sensors, fluid pressure sensors, position sensors, accelerometers, shock sensors, rotation sensors, vibration sensors, tilt sensors, pressure sensors, blood chemistry sensors, blood metabolic sensors, mechanical stress sensors and temperature sensors. Sensors can be placed at a density of greater than 1, 2, 3, 4, 5, 6, 7, 8, 9, 10 or greater than 10 sensors per square centimeter or at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter.

The above sensors may be continuously monitored in order to provide analysis of 'real-world' activity, healing, and changes in function over time, to evaluate patient activity, patient cardiac function, and to better understand the conditions which artificial heart valves are exposed to in the real world. They can be utilized to detect, monitor and report, a wide variety of metabolic parameters, including for example: Coagulation/Clotting parameters such as PT, PTT, clotting time and INR; Blood Oxygen content; Blood $CO_2$ content; Blood pH; Blood cholesterol; Blood lipids (HDL, LDL); Blood Glucose; Cardiac enzymes; Hepatic Enzymes; Electrolytes; Blood Cell Counts; and Kidney Function parameters (BUN, Creatinine, etc.). They can also be utilized to detect, monitor and report measurements of cardiac output, ejection fraction and cardiac index; permit in situ hemodynamic monitoring of parameters such as systolic and diastolic pressure, transvalvular pressure and regurgitation; and estimate parameters such systemic (or pulmonary) vascular resistance.

B. Use of Heart Valves to Deliver Therapeutic Agent(s)

As noted above, the present invention also provides drug-eluting heart valves and/or delivery devices which comprise one or more sensors, and which can be utilized to release a therapeutic agent (e.g., a drug) to a desired location within the body (e.g., into the vascular system, the vascular wall, and/or the valve leaflets). For example, anti-restenotic drugs (e.g., paclitaxel, sirolimus, or an analog or derivative of these), can be administered to an valvular lesion (such as fibrosis/pannus of the leaflets) utilizing a drug-eluting heart valve (e.g., a balloon-expandable heart valve or a drug-coated balloon heart valve as described in U.S. Pat. No. 7,491,188, U.S. Patent Application Nos. 2006/0079836, US 2009/0254063, US 2010/0023108, and US 2010/0042121). Within preferred embodiments one or more sensors (e.g., pressure sensors, contact sensors, accelerometers, and/or position sensors) can be utilized to determine appropriate placement of the desired drug, as well as the quantity of drug that is released at the desired site.

Within other embodiments of the invention a wide variety of additional therapeutic agents may be delivered (e.g., to prevent or treat an infection, such as endocarditis or infections of the valve, or to treat another disease state), including for example: Anthracyclines (e.g., gentamycin, tobramycin, doxorubicin and mitoxantrone); Fluoropyrimidines (e.g., 5-FU); Folic acid antagonists (e.g., methotrexate); Podophylotoxins (e.g., etoposide); Camptothecins; Hydroxyureas, and Platinum complexes (e.g., cisplatin) (see e.g., U.S. Pat. No. 8,372,420 which is incorporated by reference in its entirety. Other therapeutic agents include beta-lactam antibiotics (e.g., the penicillins, cephalosporins, carbacephems and carbapenems); aminoglycosides (e.g., sulfonamides, quinolones and the oxazolidinones); glycopeptides (e.g., vancomycin); lincosamides (e.g., clindamycin); lipopeptides; macrolides (e.g., azithromycin); monobactams; nitrofurans; polypeptides (e.g, bacitracin); and tetracyclines.

C. Use of Heart Valves Having Sensors to Measure Flow, and Flow Obstruction

As noted above, within various aspects of the present invention heart valves and associated delivery devices can be utilized to measure blood flow across a valve and determine if flow rates are normal or an obstruction is present.

Hence, within one embodiment of the invention drainage heart valves are provided with one or more sensors that can measure pressure change, fluid (blood) flow, and/or fluid (blood) volume. They can be utilized to determine circulation through the heart, and in certain embodiments to advise a health care provider of impending stenosis, blockage, or regurgitation of the heart valve.

D. Methods for Monitoring Infection in Heart Valves

Within other embodiments heart valves are provided comprising one or more temperature sensors. Such heart valves can be utilized to measure the temperature of the heart valve, the blood, and in the local tissue adjacent to the heart valve. Methods are also provided for monitoring changes in temperature over time, in order to determine and/or provide notice (e.g., to a patient and/or a healthcare provider) that an infection may be imminent.

In certain embodiments of the present invention, metabolic and physical sensors can also be placed on or within the various components of a mechanical, biological or percutaneous heart valve in order to monitor for rare, but potentially life-threatening complications of heart valves. In some patients, the heart valve leaflets (endocarditis; infection of the valve leafletsntypically with bacterial "vegetations" of infectious material) and surrounding tissues (endocarditis of the lining of the heart and/or myocarditis in the heart muscle) can become infected; typically from bacteria colonizing the patient's own skin (contamination during surgery or administration of i.v. fluids and drugs) or oral mucosa (contamination during dental work) that enter the blood stream and colonize the artificial valves (often *Streptococci, Staphylococcus aureus* or *Staphylococcus epidermidis;* occasionally *Aspergillus* species, *Brucella* species, *Enterococcus, Pseudomonas, Coxiella burnetii, Chlamydia* species, viruses, and HACEK bacteria). Sensors such as temperature sensors (detecting temperature increases), pH sensors (detecting pH decreases), bacterial DNA sensors, and other metabolic sensors can be used to suggest the presence of infection on or around the artificial valve. For example, temperature sensors and/or bacterial DNA sensors may be included within one or more components of a prosthetic heart valve in order to allow early detection of infection which could allow preemptive treatment with antibiotics and reduce the probability of valve damage and other complications (e.g. septic emboli).

Hence, within one embodiment of the invention methods are provided for determining an infection associated with a heart valve (e.g., a prosthetic heart valve), comprising the steps of a) providing to a subject a heart valve as described herein, wherein the heart valve comprises at least one temperature sensor, bacterial DNA sensor, and/or metabolic sensor, and b) detecting a change in said temperature sensor, bacterial DNA sensor, and/or metabolic sensor, and thus determining the presence of an infection (endocarditis). Within various embodiments of the invention the step of detecting may be a series of detections over time, and a change in the sensor is utilized to assess the presence or development of an infection. Within further embodiments a change of 0.5%, 1.0%, or 1.5% elevation of temperature or a bacterial DNA marker and/or a metabolic factor over time (e.g., 0.5, 1.0, 1.5, 2.0, 2.5, 3.0, 3.5, 4 hours, 12 hours, 1 day, or 2 days) can be indicative of the presence of an infection (or a developing infection).

Within various embodiments of the invention an antibiotic may be delivered in order to prevent, inhibit or treat an infection subsequent to its detection. Representative examples of suitable antibiotics are well known, and are described above under Section B (the "Therapeutic Agents")

E. Further Uses of Sensor-Containing Heart Valves in Healthcare

Sensors on heart valves, and any associated medical devices have a variety of benefits in the healthcare setting, and in non-healthcare settings (e.g., at home or work). For example, postoperative progress can be monitored (readings compared from day-to-day, week-to-week, etc.) and the information compiled and relayed to both the patient and the attending physician allowing rehabilitation to be followed sequentially and compared to expected (typical population) norms. Within certain embodiments, a wearable device interrogates the sensors on a selected or randomized basis, and captures and/or stores the collected sensor data. This data may then be downloaded to another system or device (as described in further detail below).

Integrating the data collected by the sensors described herein (e.g., contact sensors, position sensors, strain gauges and/or accelerometers) with simple, widely available, commercial analytical technologies such as pedometers and global positioning satellite (GPS) capability, allows further clinically important data to be collected such as, but not restricted to: extent of patient ambulation (time, distance, steps, speed, cadence), patient activity levels (frequency of activity, duration, intensity), exercise tolerance (work, calories, power, training effect), cardiac function and heart valve performance under various "real world" conditions. It is difficult to overstate the value of this information in enabling better management of the patient's recovery. An attending physician (or physiotherapist, rehabilitation specialist) only observes the patient episodically during scheduled visits; the degree of patient function at the exact moment of examination can be impacted by a multitude of disparate factors such as: the presence or absence of pain, the presence or absence of inflammation of the sternotomy site, time of day, compliance and timing of medication use (pain medications, anti-inflammatories), recent activity, patient strength, mental status, language barriers, the nature of their doctor-patient relationship, or even the patient's ability to accurately articulate their symptoms—to name just a few. Continuous monitoring and data collection can allow the patient and the physician to monitor progress objectively by supplying objective information about patient function under numerous conditions and circumstances, to evaluate how performance has been affected by various interventions (heart medications, pain control, anti-inflammatory medication, rest, etc.), and to compare patient progress versus previous function and future expected function. Better therapeutic decisions and better patient compliance can be expected when both the doctor and the patient have the benefit of observing the impact of various treatment modalities on patient rehabilitation, activity, function and overall performance.

F. Generation of Power

Within certain aspects of the invention, a small electrical generation unit can be positioned along an outer, or alternatively an inner, surface of the heart valve. Briefly, a variety of techniques have been described for scavenging power from small mechanical movements (such as those generated by a heart beat) or mechanical vibration (such as that generated by blood flow). See, for example, the article entitled "Piezoelectric Power Scavenging of Mechanical Vibration Energy," by U.K. Singh et al., as published in the Australian Mining Technology Conference, Oct. 2-4, 2007, pp. 111-118, and the article entitled "Next Generation Micro-power Systems by Chandrakasan et al., as published in the 2008 Symposium on VLSI Circuits Digest of Technical Papers, pp. 1-5. See also U.S. Pat. No. 8,283,793 entitled "Device for Energy Harvesting within a Vessel," and U.S. Pat. No. 8,311,632 entitled "Devices, Methods and Systems for Harvesting Energy in the Body," all of the above of which are incorporated by reference in their entirety. These references provide examples of different types of power scavengers which can produce electricity from very small motion and store the electricity for later use. The above references also describes embodiments in which pressure is applied and released from the particular structure in order to produce electricity without the need for motion, but rather as a result of the application of high pressure. In addition, these references describe embodiments wherein electricity can be produced from pulsatile forces, such as those found within a variety of structures within the body (e.g., within the heart or arterial systems).

After the electricity is generated by one or more generators, the electricity is transmitted to any one of the variety of sensors which is described herein. For example, it can be transmitted to the sensors 22 shown in FIGS. 15, 16, and/or 17 (including for example, contact sensors 22B, position sensors 24, pressure sensors 42 and/or temperature sensors 46). It may also be transmitted to the other sensors described herein. The transmission of the power can be carried out by any acceptable technique. For example, if the sensor is physically coupled to the implant, electric wires may run from the generator to the particular sensor. Alternatively, the electricity can be transmitted wirelessly in the same way that wireless smartcards receive power from closely adjacent power sources using the appropriate send and receive antennas. Such send and receive techniques of electric power are also described in the publication and the patent applications and issued U.S. patent previously described, all of which are incorporated herein by reference.

G. Medical Imaging and Self-Diagnosis of Assemblies Comprising Heart Valves; Predictive Analysis and Predictive Maintenance Within other aspects of the invention methods are provided for imaging a heart valve and/or an associated delivery devices (e.g., a guidewire, catheter, balloon catheter) as provided herein, comprising the steps of (a) detecting the location of one or more sensors in a heart valve, and/or associated medical devices; and (b) visually displaying the location of said one or more sensors, such that an image of the heart valve and/or the associated delivery devices is created. Within various embodiments, the step of detecting may be done over time, and the visual display may thus show positional movement over time. Within certain preferred embodiments the image which is displayed is a three-dimensional image. Within other embodiment, the imaging techniques may be utilized post-operatively in order to examine the heart valve, and/or to compare operation (valvular function) and/or movement (migration) of the device over time.

The present invention provides heart valves and associated medical devices which are capable of imaging through the use of sensors over a wide variety of conditions. For example, within various aspects of the invention methods are provided for imaging a heart valve [or portion thereof (e.g., a medical device or kit as described herein)] or an assembly comprising a heart valve, delivery device (e.g. guidewire, catheter, balloon catheter, anchoring device) or kit (as described herein) with sensors, comprising the steps of detecting the changes in sensors in, on, and or within a heart valve, delivery device (e.g. guidewire, catheter, balloon catheter, anchoring device) or kit over time, and wherein the heart valve, delivery device (e.g. guidewire, catheter, balloon catheter, anchoring device) or kit comprises sensors at a density of greater than 1, 2, 3, 4, 5, 6, 7, 8, 9, 10 or greater than 10 sensors per square centimeter. Within other aspects the heart valve, delivery device (e.g. guidewire, catheter, balloon catheter, anchoring device), or kit comprises sensors at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter. Within various embodiments, at least one or more of the sensors may be placed randomly, or at one or more specific locations within the heart valve, delivery device (e.g. guidewire, catheter, balloon catheter, anchoring device), or kit as described herein. As noted above, a wide variety of sensors can be utilized therein, including for example, contact sensors, strain gauge sensors, pressure sensors, fluid pressure sensors, position sensors, pulse pressure sensors, liquid (e.g., blood) volume sensors, liquid (e.g., blood) flow sensors, liquid (e.g., blood) chemistry sensors, liquid (e.g., blood) metabolic sensors, mechanical stress sensors, and temperature sensors.

For example, a heart valve, delivery device (e.g. guidewire, catheter, balloon catheter, anchoring device), or kit comprising sensors as described herein can be utilized to image anatomy through sensors which can detect positional movement. The sensors used can also include accelerometers and motion sensors to detect movement/position of the heart valve during percutaneous placement and the movement/position of the valve leaflets after implantation. Changes in the position of the accelerometers and/or motion sensors over time can be used as a measurement of changes in the position of the heart valve over time (during and after placement). Such positional changes can be used as a surrogate marker of heart valve anatomy—i.e. they can form an "image" of the heart valve to provide information on the movement, function and performance of the heart valve (particularly the leaflets), and/or heart valve movement/migration from the site of implantation.

Certain exemplary embodiments will now be explained in more detail. One particular benefit is the live and in-situ monitoring of the patient's recovery and the implanted heart valve 10. The sensors as described herein are collecting data on a constant basis, during normal daily activities and even during the night if desired. For example, the contact sensors can obtain and report data once every 10 seconds, once a minute, or once a day. Other sensors will collect data more frequently, such as several times a second. For example, it would be expected that the temperature, pressure, flow, and/or position data would be collected and stored several times a second. Other types of data might only need to be collected by the minute or by the hour. Still other sensors may collect data only when signaled by the patient to do so (via an external signaling/triggering device) as part of "event recording"—i.e. when the patient experiences a particular event (e.g. chest pain, light-headedness, shortness of breath, etc.)—and signals the device to obtain a reading at that time in order to allow the comparison of subjective/symptomatic data to objective/sensor data in an effort to better understand the underlying cause or triggers of the patient's symptoms.

In certain instances the heart valve (e.g. mechanical, biologic or percutaneous heart valve) is of sufficient size and has more than sufficient space in order to house one or more processor circuits, CPUs, memory chips and other electrical circuits as well as antennas for sending and receiving the data. Within other embodiments, the associated delivery devices (e.g. guidewire, catheter, balloon catheter, anchoring device) may be able to house the one or more processor circuits, CPUs, memory chips and other electrical circuits as well as antennas for sending and receiving the data. Processors can be programmed to collect data from the various sensors on any desired schedule as set by the medical professional. All activity can be continuously monitored post operation or post-procedure and the data collected and stored in the memory located inside the implant.

A patient will generally have regular medical checkups. When the patient goes to the doctor's office for a medical checkup, the doctor will bring a reading device closely adjacent to the heart valve 10, in this example a mechanical heart valve, in order to transfer the data from the internal circuit inside the implant to the database in the physician's office. The use of wireless transmission using smartcards or other techniques is very well known in the art and need not be described in detail. Examples of such wireless transmission of data are provided in the published patent applications and patents which have been described herein. The data which has been collected (e.g., over a short period of time, over several weeks or even several months) is transferred in a few moments from the memory which is positioned in the implant to the doctor's computer or wireless device. The computer then analyzes the data for anomalies, unexpected changes over time, positive or negative trends, and other signs which may be indicative of the health of the patient, cardiac function of the patient, and the operability/function of the heart valve. For example, if the patient has decided to go walking or jogging, the doctor will be able to monitor the effect of such activity on the heart valve 10, including the accelerations (increase in heart rate) and strains (increase in cardiac output) during the event itself. The doctor can then look at the health of the heart valve in the hours and days after the event and compare it to data prior to the event to determine if any particular event caused long term damage, or if the activities subjected the heart valve to forces beyond the manufacturer's performance specifications for that particular heart valve. Data can be collected and compared with respect to the ongoing and long term performance of the heart valve from the strain gauges, flow sensors, pressure sensors, the contact sensors, the surface wear sensors, or other sensors which may be present.

In one alternative, the patient may also have such a reading device in their home which collates the data from the heart valve on a periodic basis, such as once per day or once per week. As described above, the patient may also be able to "trigger" a device reading (via an external signaling/triggering device) as part of "event recording." For example, within certain embodiments the prosthetic heart valves provided herein can instruct or otherwise notify the patient, or a permitted third-party as to deviations (e.g., greater than 10%, 20%, 25%, 50%, 70%, and or 100%) from normal, and/or, set parameters. Empowering the patient to follow their own rehabilitation—and enabling them to see the positive (and negative) effects of various lifestyle choices on their health and rehabilitation—can be expected to improve compliance and improve patient outcomes. Furthermore, their experience can be shared via the web with other patients to compare their progress versus expected "norms" for function and rehabilitation and alert them to signs and symptoms that should be brought to their doctor's attention. The performance of different implants can be compared in different patients (different sexes, weights, activity levels, etc.) to help manufacturers design better devices and assist surgeons and other healthcare providers in the selection of the right heart valve for specific patient types. Payers, patients, manufacturers and physicians could all benefit from the collection of this comparative information. Lastly, data accumulated at home can be collected and transmitted via the Internet to the physician's office for analysis— potentially eliminating unnecessary visits in some cases and encouraging immediate medical follow-up in others.

H. Methods of Monitoring Assemblies Comprising Heart Valves

Figure 15:
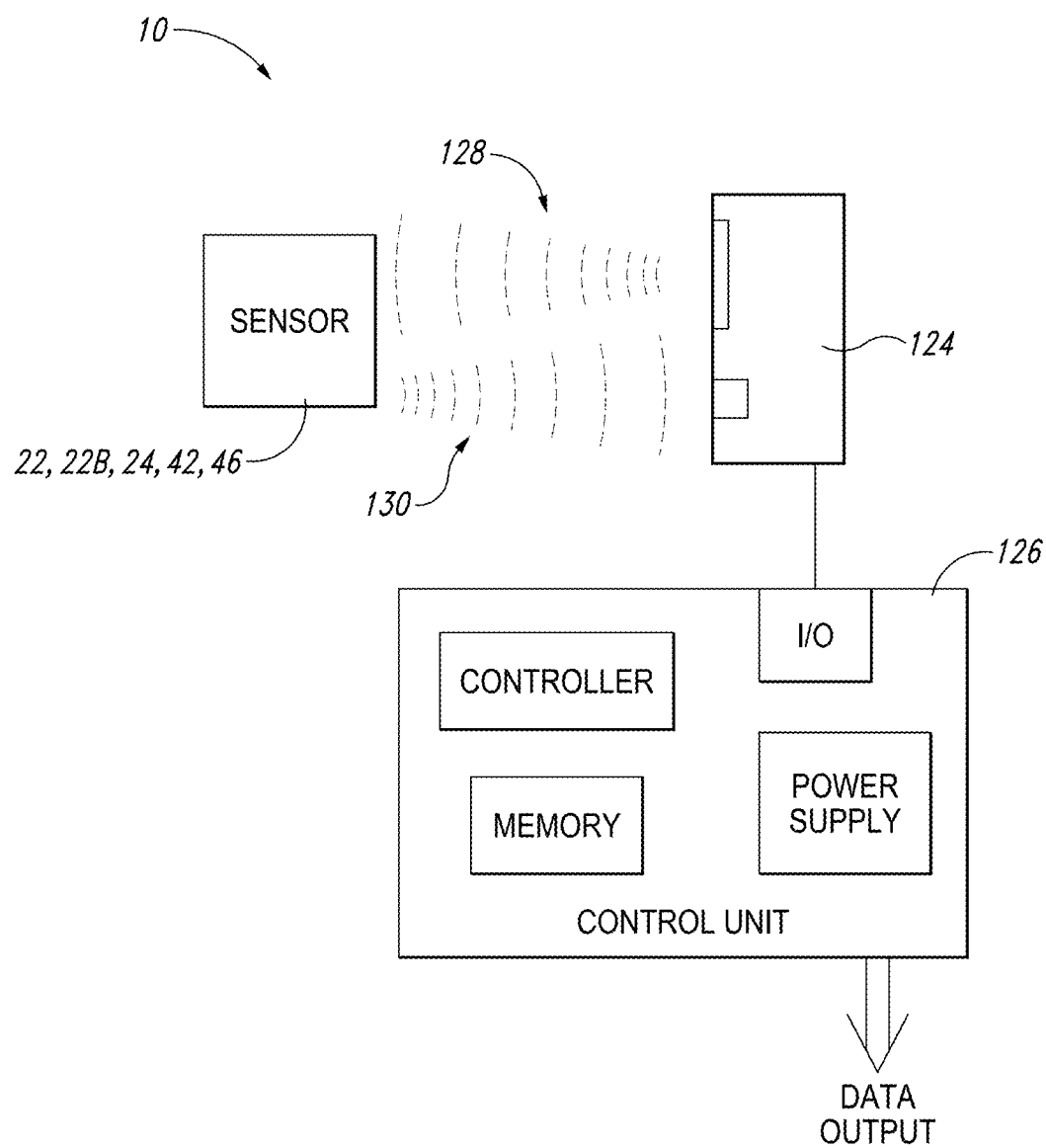
FIG. 15 illustrates an information and communication technology system embodiment arranged to process sensor data.

As noted above, the present invention also provides methods for monitoring one or more of the heart valve and/or heart valve delivery device (e.g. guidewire, catheter, balloon catheter, anchoring device) assemblies provided herein. For example, FIG. 15 illustrates a monitoring system usable with the heart valve 10 as of the type shown in any one of the Figures described above. The monitoring system includes one or more sensors 22 (including, for example, contact sensors 22B, position sensors 24, pressure sensors 42, and/or temperature sensors 46) an interrogation module 124, and a control unit 126. The sensor (e.g., 22, 26, 27 and/or 28) can be passive, wireless type which can operate on power received from a wireless source. Such sensors of this type are well known in the art and widely available. A pressure sensor of this type might be a MEMS pressure sensor, for example, Part No. LPS331AP, sold on the open market by STMicroelectronics. MEMS pressure sensors are well known to operate on very low power and suitable to remain unpowered and idle for long periods of time. They can be provided power wirelessly on an RF signal and, based on the power received wirelessly on the RF signal, perform the pressure sensing and then output the sensed data.

In one embodiment, an electrical generation system (as described above) is provided that can be utilized to power the sensors described herein. During operation, as shown in FIG. 15, an interrogation module 124 outputs a signal 128. The signal 128 is a wireless signal, usually in the RF band, that contains power for the sensors 22 as well as an interrogation request that the sensors perform a sensing. Upon being interrogated with the signal 128, the sensors 22 powers up and stores power in onboard capacitors sufficient to maintain operation during the sensing and data reporting. Such power receiving circuits and storing on onboard capacitors are well known in the art and therefore need not be shown in detail. The appropriate sensing is carried out by the sensors 22 and then the data is output from the sensor back to the interrogation module 124 on a signal 130, where it is received at an input port of the integration module.

According to one embodiment, sufficient signal strength is provided in the initial signal 128 to provide power for the sensor and to carry out the sensing operation and output the signal back to the interrogation module 124. In other embodiments, two or more signals 128 are sent, each signal providing additional power to the sensor to permit it to complete the sensing operation and then provide sufficient power to transfer the data via the signal path 130 back to the interrogation module 124. For example, the signal 128 can be sent continuously, with a sensing request component at the first part of the signal and then continued providing, either as a steady signal or pulses to provide power to operate the sensor. When the sensor is ready to output the data, it sends a signal alerting the interrogation module 124 that data is coming and the signal 128 can be turned off to avoid interference. Alternatively, the integration signal 128 can be at a first frequency and the output signal 130 at a second frequency separated sufficiently that they do not interfere with each other. In a preferred embodiment, they are both the same frequency so that the same antenna on the sensor can receive the signal 128 and send signal 130.

The interrogation signal 128 may contain data to select specific sensors on the heart valve and/or the heart valve delivery device (e.g. guidewire, catheter, balloon catheter, anchoring device). For example, the signal 128 may power up all sensors on the heart valve (or delivery device at the time of implantation of a percutaneous valve) at the same time and then send requests for data from each at different selected times so that with one interrogation signal 128 provided for a set time, such as 1-2 seconds, results in each of the sensors on the heart valve (and/or delivery device) collecting data during this time period and then, at the end of the period, reporting the data out on respective signals 130 at different times over the next 0.5 to 2 seconds so that with one interrogation signal 128, the data from all sensors 22 is collected.

The interrogation module 124 is operating under control of the control unit 126 which has a microprocessor for the controller, a memory, an I/O circuit to interface with the interrogation module and a power supply. The control unit may output data to a computer or other device for display and use by the physician to treat the subject.

Figure 16:
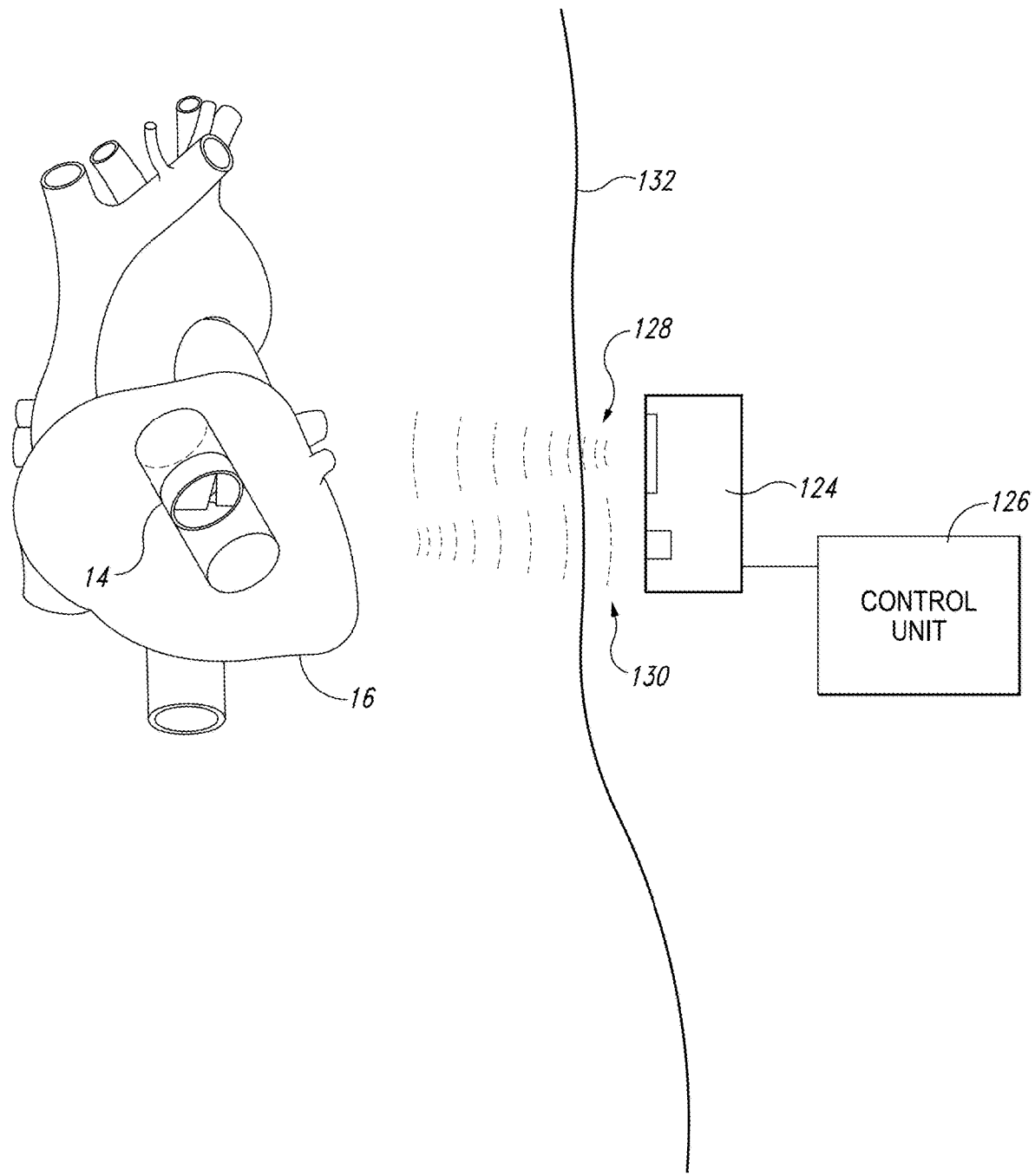
FIG. 16 is a block diagram of a sensor, interrogation module, and a control unit according to one embodiment of the invention.

FIG. 16 illustrates the operation according to a preferred embodiment within a subject. The subject has an outer skin 132. As illustrated in FIG. 13, the interrogation module 124 and control unit 126 are positioned outside the skin 132 of the subject. The interrogation signal 128 passes through the skin of the subject with a wireless RF signal, and the data is received on a wireless RF signal 130 from the sensors within the balloon heart valve 14, which is positioned within the heart 16, back to the interrogation module 124. While the wireless signal can be in any frequency range, an RF range is preferred. A frequency in the VLF to LF ranges of between 3-1300 kHz is preferred to permit the signal to be carried to sufficient depth inside the body with low power, but frequencies below 3 kHz and above 1300 kHz can also be used. The sensing does not require a transfer of large amounts of data and low power is preferred; therefore, a low frequency RF signal is acceptable. This also avoids competition from an inadvertent activation by other wireless signal generators, such as blue tooth, cell phones and the like.

Figure 17:
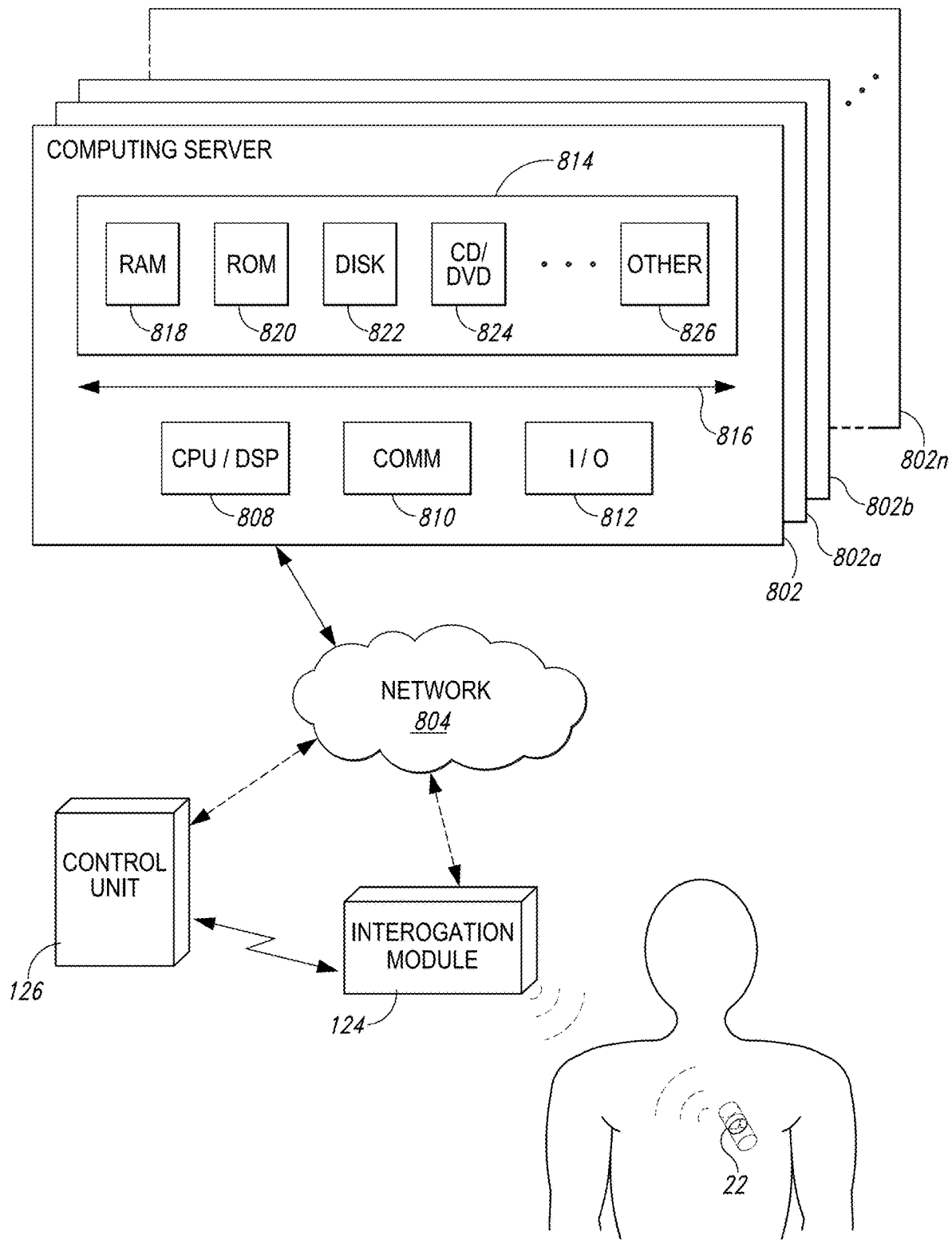
FIG. 17 is a schematic illustration of one or more sensors positioned on a heart valve within a subject which is being probed for data and outputting data, according to one embodiment of the invention.

I. Collection, Transmission, Analysis, and Distribution of Data from Assemblies Comprising Heart Valves FIG. 17 illustrates one embodiment of an information and communication technology (ICT) system 800 arranged to process sensor data (e.g., data from the sensors 22). In FIG. 17, the ICT system 800 is illustrated to include computing devices that communicate via a network 804, however in other embodiments, the computing devices can communicate directly with each other or through other intervening devices, and in some cases, the computing devices do not communicate at all. The computing devices of FIG. 17 include computing servers 802, control units 126, interrogation units 124, and other devices that are not shown for simplicity.

In FIG. 17, one or more sensors 22 communicate with an interrogation module 124. The interrogation module 124 of FIG. 17 is directed by a control unit 126, but in other cases, interrogation modules 124 operates autonomously and passes information to and from sensors 22. One or both of the interrogation module 124 and control unit 126 can communicate with the computing server 802.

Within certain embodiments, the interrogation module and/or the control unit may be a wearable device on the subject. The wearable device (e.g., a watch-like device, a wrist-band, glasses, or other device that may be carried or worn by the subject) can interrogate the sensors over a set (or random) period of time, collect the data, and forward the data on to one or more networks (804). Furthermore, the wearable device may collect data of its own accord which can also be transmitted to the network. Representative examples of data that may be collected include location (e.g., a GPS), body or skin temperature, and other physiologic data (e.g., pulse, ECG, respiratory rate). Within yet other embodiments, the wearable device may notify the subject directly of any of a number of prescribed conditions, including but not limited to possible or actual failure of the device.

The information that is communicated between an interrogation module 124 and the sensors 22, may be useful for many purposes as described herein. In some cases, for example, sensor data information is collected and analyzed expressly for the health of an individual subject. In other cases, sensor data is collected and transmitted to another computing device to be aggregated with other data (for example, the sensor data from 22 may be collected and aggregated with other data collected from a wearable device (e.g., a device that may, in certain embodiments, include GPS data and the like).

FIG. 17 illustrates aspects of a computing server 802 as a cooperative bank of servers further including computing servers 802a, 802b, and one or more other servers 802n. It is understood that computing server 802 may include any number of computing servers that operate individually or collectively to the benefit of users of the computing servers.

In some embodiments, the computing servers 802 are arranged as cloud computing devices created in one or more geographic locations, such as the United States and Canada. The cloud computing devices may be created as MICROSOFT AZURE cloud computing devices or as some other virtually accessible remote computing service.

An interrogation module 124 and a control unit 126 are optionally illustrated as communicating with a computing server 802. Via the interrogation module 124 or control unit 126, sensor data is transferred to (and in addition or alternatively from) a computing server 802 through network 804.

The network 804 includes some or all of cellular communication networks, conventional cable networks, satellite networks, fiber-optic networks, and the like configured as one or more local area networks, wide area networks, personal area networks, and any other type of computing network. In a preferred embodiment, the network 804 includes any communication hardware and software that cooperatively works to permit users of computing devices to view and interact with other computing devices.

Computing server 802 includes a central processing unit (CPU) digital signal processing unit (DSP) 808, communication modules 810, Input/Output (I/O) modules 812, and storage module 814. The components of computing server 802 are cooperatively coupled by one or more buses 816 that facilitate transmission and control of information in and through computing server 802. Communication modules 810 are configurable to pass information between the computer server 802 and other computing devices (e.g., computing servers 802a, 802b, 802n, control unit 126, interrogation unit 124, and the like). I/O modules 812 are configurable to accept input from devices such as keyboards, computer mice, trackballs, and the like. I/O modules 812 are configurable to provide output to devices such as displays, recorders, LEDs, audio devices, and the like.

Storage module 814 may include one or more types of storage media. For example, storage module 814 of FIG. 17 includes random access memory (RAM) 818, read only memory (ROM) 810, disk based memory 822, optical based memory 8124, and other types of memory storage media 8126. In some embodiments one or more memory devices of the storage module 814 has configured thereon one or more database structures. The database structures may be used to store data collected from sensors 22.

In some embodiments, the storage module 814 may further include one or more portions of memory organized a non-transitory computer-readable media (CRM). The CRM is configured to store computing instructions executable by a CPU 808. The computing instructions may be stored as one or more files, and each file may include one or more computer programs. A computer program can be standalone program or part of a larger computer program. Alternatively or in addition, each file may include data or other computational support material for an application that directs the collection, analysis, processing, and/or distribution of data from sensors (e.g., heart valve sensors). The sensor data application typically executes a set of instructions stored on computer-readable media.

It will be appreciated that the computing servers shown in the figures and described herein are merely illustrative and are not intended to limit the scope of the present invention. Computing server 802 may be connected to other devices that are not illustrated, including through one or more networks such as the Internet or via the Web that are incorporated into network 804. More generally, a computing system or device (e.g., a "client" or "server") or any part thereof may comprise any combination of hardware that can interact and perform the described types of functionality, optionally when programmed or otherwise configured with software, including without limitation desktop or other computers, database servers, network storage devices and other network devices, PDAs, cell phones, glasses, wrist bands, wireless phones, pagers, electronic organizers, Internet appliances, television-based systems (e.g., using set-top boxes and/or personal/digital video recorders), and various other products that include appropriate inter-communication capabilities. In addition, the functionality provided by the illustrated system modules may in some embodiments be combined in fewer modules or distributed in additional modules. Similarly, in some embodiments the functionality of some of the illustrated modules may not be provided and/or other additional functionality may be available.

In addition, while various items are illustrated as being stored in memory or on storage while being used, these items or portions of them can be transferred between memory and other storage devices for purposes of memory management and/or data integrity. In at least some embodiments, the illustrated modules and/or systems are software modules/systems that include software instructions which, when executed by the CPU/DSP 808 or other processor, will program the processor to automatically perform the described operations for a module/system. Alternatively, in other embodiments, some or all of the software modules and/or systems may execute in memory on another device and communicate with the illustrated computing system/device via inter-computer communication.

Furthermore, in some embodiments, some or all of the modules and/or systems may be implemented or provided in other manners, such as at least partially in firmware and/or hardware means, including, but not limited to, one or more application-specific integrated circuits (ASICs), standard integrated circuits, controllers (e.g., by executing appropriate instructions, and including microcontrollers and/or embedded controllers), field-programmable gate arrays (FPGAs), complex programmable logic devices (CPLDs), and the like. Some or all of the systems, modules, or data structures may also be stored (e.g., as software instructions or structured data) on a transitory or non-transitory computer-readable storage medium 814, such as a hard disk 822 or flash drive or other non-volatile storage device 8126, volatile 818 or non-volatile memory 810, a network storage device, or a portable media article (e.g., a DVD disk, a CD disk, an optical disk, a flash memory device, etc.) to be read by an appropriate input or output system or via an appropriate connection. The systems, modules, and data structures may also in some embodiments be transmitted as generated data signals (e.g., as part of a carrier wave or other analog or digital propagated signal) on a variety of computer readable transmission mediums, including wireless-based and wired/cable-based mediums. The data signals can take a variety of forms such as part of a single or multiplexed analog signal, as multiple discrete digital packets or frames, as a discrete or streaming set of digital bits, or in some other form. Such computer program products may also take other forms in other embodiments. Accordingly, the present invention may be practiced with other computer system configurations.

In FIG. 17, sensor data from, e.g., sensors 22 is provided to computing server 802. Generally speaking, the sensor data, represents data retrieved from a known subject and from a known sensor. The sensor data may possess include or be further associated with additional information such as the USI, UDI, a time stamp, a location (e.g., GPS) stamp, a date stamp, and other information. The differences between various sensors is that some may include more or fewer data bits that associate the data with a particular source, collection device, transmission characteristic, or the like.

In some embodiments, the sensor data may comprise sensitive information such as private health information associated with a specific subject. Sensitive information, for example sensor data from sensors e.g., 22, may include any information that an associated party desires to keep from wide or easy dissemination. Sensitive information can stand alone or be combined with other non-sensitive information. For example, a subject's medical information is typically sensitive information. In some cases, the storage and transmission of a subject's medical information is protected by a government directive (e.g., law, regulation, etc.) such as the U.S. Health Insurance Portability and Accountability Act (HIPPA).

As discussed herein, a reference to "sensitive" information includes information that is entirely sensitive and information that is some combination of sensitive and non-sensitive information. The sensitive information may be represented in a data file or in some other format. As used herein, a data file that includes a subject's medical information may be referred to as "sensitive information." Other information, such as employment information, financial information, identity information, and many other types of information may also be considered sensitive information.

A computing system can represent sensitive information with an encoding algorithm (e.g., ASCII), a well-recognized file format (e.g., PDF), or by some other format. In a computing system, sensitive information can be protected from wide or easy dissemination with an encryption algorithm.

Generally speaking, sensitive information can be stored by a computing system as a discrete set of data bits. The set of data bits may be called "plaintext." Furthermore, a computing system can use an encryption process to transform plaintext using an encryption algorithm (i.e., a cipher) into a set of data bits having a highly unreadable state (i.e., cipher text). A computing system having knowledge of the encryption key used to create the cipher text can restore the information to a plaintext readable state. Accordingly, in some cases, sensitive data (e.g., sensor data 806a, 806b) is optionally encrypted before being communicated to a computing device.

In one embodiment, the operation of the information and communication technology (ICT) system 800 of FIG. 17 includes one or more sensor data computer programs stored on a computer-readable medium. The computer program may optionally direct and/or receive data from one or more heart valve sensors implanted in one or more subjects. A sensor data computer program may be executed in a computing server 802. Alternatively, or in addition, a sensor data computer program may be executed in a control unit 126, an interrogation unit 124.

In one embodiment, a computer program to direct the collection and use of heart valve sensor data is stored on a non-transitory computer-readable medium in storage module 814. The computer program is configured to identify a subject who has a wireless heart valve inserted in his or her body. The wireless heart valve may include one or more wireless sensors.

In some cases, the computer program identifies one subject, and in other cases, two or more subjects are identified. The subjects may each have one or more wireless heart valves, and each wireless heart valve may have one or more wireless sensors of the type described herein.

The computer program is arranged to direct the collection of sensor data from the wireless heart valve devices. The sensor data is generally collected with a wireless interrogation unit 124. In some cases, the program communicates with the wireless interrogation unit 124. In other cases, the program communicates with a control unit 126, which in turn directs a wireless interrogation unit 124. In still other cases, some other mechanism is used direct the collection of the sensor data.

Once the sensor data is collected, the data may be further processed. For example, in some cases, the sensor data includes sensitive subject data, which can be removed or disassociated with the data. The sensor data can be individually stored (e.g., by unique sensor identification number, device number, etc.) or aggregated together with other sensor data by sensor type, time stamp, location stamp, date stamp, subject type, other subject characteristics, or by some other means.

The following pseudo-code description is used to generally illustrate one exemplary algorithm executed by a computing server 802 and generally described herein with respect to FIG. 17:

```
Start
   Open a secure socket layer (SSL)
   Identify a subject
   Communicate with a predetermined control unit
   Request sensor data from the subject via the control unit
   Receive sensor data
   If the sensor data is encrypted
       THEN decrypt the sensor data
   Store encrypted data in the selected storage locations
   Aggregate the sensor data with other sensor data
   Store encrypted data in the selected storage locations
   Maintain a record of the storage transaction
   Perform post storage actions
End
```

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., AT&T, T-Mobile, Verizon), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

In conclusion, heart valves utilizing a variety of sensors can be utilized to serve a variety of critical clinical functions, such as safe, accurate and less traumatic placement and deployment of the heart valve, procedural and post-operative "real time" imaging of heart valve and the surrounding anatomy, the development of heart valve complications, and the patient's overall health and cardiac status. Currently, post-operative (both in hospital and out-patient) evaluation of heart valve patients is through patient history, physical examination and medical monitoring that is supplemented with diagnostic imaging studies as required. However, most of the patient's recuperative period occurs between hospital and office visits and the majority of data on daily function goes uncaptured; furthermore, monitoring patient progress through the use of some diagnostic imaging technology can be expensive, invasive and carry its own health risks (the use of nuclear isotopes or certain dyes). It can, therefore, be very difficult to accurately measure and follow the development or worsening of symptoms and evaluate "real life" heart valve performance, particularly as they relate to patient activity levels, exercise tolerance, and the effectiveness of rehabilitation efforts and medications.

At present, neither the physician nor the patient has access to the type of "real time," continuous, objective, heart valve performance measurements that they might otherwise like to have. Being able to monitor in situ heart valve function, integrity, anatomy and physiology can provide the physician with valuable objective information during office visits; furthermore, the patient can take additional readings at home at various times (e.g. when experiencing chest pain, during exercise, after taking medications, etc.) to provide important complementary clinical information to the doctor (which can be sent to the healthcare provider electronically even from remote locations). From the perspective of the patient, being able to monitor many of these same parameters at home allows them to take a more proactive role in their care and recovery and provide him or her with either an early warning indicator to seek medical assistance or with reassurance.

In one alternative, the patient may have a reading device in their home which collates the data from the heart valve on a periodic basis, such as once per day or once per week. In addition to empowering the patient to follow their own rehabilitation—and enabling them to see the positive (and negative) effects of various lifestyle choices on their health and rehabilitation—such information access can be expected to improve compliance and improve patient outcomes. For example, within certain embodiments the devices and systems provided herein can instruct and/or notify the patient, or a permitted third-party as to deviations (e.g., greater than 10%, 20%, 25%, 50%, 70%, and or 100%) from normal, and/or, set parameters. Furthermore, their recovery experience can be shared via the web with other patients to compare their progress versus expected "norms" for function and rehabilitation and alert them to signs and symptoms that should be brought to their doctor's attention. From a public health perspective, the performance of different heart valves (and heart valve types; for example mechanical versus biological valves) can be compared in different patients (different sexes, disease severity, activity levels, concurrent diseases such as hypertension and diabetes, smoking status, obesity, etc.) to help manufacturers design better heart valves and assist physicians in the selection of the right heart valve for specific patient types. Payers, patients, manufacturers and physicians could all benefit from the collection of this comparative information. Poor and dangerous products could be identified and removed from the market and objective long-term effectiveness data collected and analyzed. Lastly, data accumulated at home can be collected and transmitted via the Internet to the physician's office for analysis—potentially eliminating unnecessary visits in some cases and encouraging immediate medical follow-up in others.

Conventions

In general, and unless otherwise specified, all technical and scientific terms used herein shall have the same meaning as those commonly understood by one of ordinary skill in the art to which the embodiment pertains. For convenience, the meanings of selected terms are provided below, where these meanings are provided in order to aid in describing embodiments identified herein. Unless stated otherwise, or unless implicit from the context in which the term is used, the meanings provided below are the meanings intended for the referenced term.

Embodiment examples or feature examples specifically provided are intended to be exemplary only, that is, those examples are non-limiting on an embodiment. The term "e.g." (latin, exempli gratia) is used herein to refer to a non-limiting example, and effectively means "for example".

Singular terms shall include pluralities and plural terms shall include the singular, unless otherwise specified or required by context. For example, the singular terms "a", "an" and "the" include plural referents unless the context clearly indicates otherwise. Similarly, the term "or" is intended to include "and" unless the context clearly indicates otherwise.

Except in specific examples provided herein, or where otherwise indicated, all numbers expressing quantities of a component should be understood as modified in all instances by the term "about", where "about" means ±5% of the stated value, e.g., 100 refers to any value within the range of 95-105.

The terms comprise, comprising and comprises are used to identify essential features of an embodiment, where the embodiment may be, for example, a composition, device, method or kit. The embodiment may optionally contain one or more additional unspecified features, and so the term comprises may be understood to mean includes.

The following are some specific numbered embodiments of the systems and processes disclosed herein. These embodiments are exemplary only. It will be understood that the invention is not limited to the embodiments set forth herein for illustration, but embraces all such forms thereof as come within the scope of the above disclosure.

1) A heart valve comprising:
a heart valve and one or more sensors positioned within or upon said heart valve.

2) The heart valve of embodiment 1 wherein said one or more sensors includes a sensor within the matrix of the heart valve.

3) The heart valve of embodiment 1 wherein said one or more sensors includes a sensor within or upon said heart valve.

4) The heart valve according to any one of embodiments 1 to 4 wherein said sensor is selected from the group consisting of fluid pressure sensors, contact sensors, position sensors, pulse pressure sensors, liquid volume sensors, liquid flow sensors, chemistry sensors, metabolic sensors, accelerometers, mechanical stress sensors and temperature sensors.

5) The heart valve according to any one of embodiments 1 to 4 wherein said heart valve is a mechanical heart valve.

6) The heart valve according to embodiment 5 wherein said mechanical valve is a ball and cage valve.

7) The heart valve according to embodiment 5 wherein said mechanical valve is a tilting disc heart valve.

8) The heart valve according to any one of embodiments 1 to 4 wherein said heart valve is a biological heart valve.

9) The heart valve according to any one of embodiments 1 to 4 wherein said heart valve is a percutaneous heart valve.

10) A medical device, comprising a percutaneous heart valve according to embodiment 9, and a balloon catheter comprising one or more sensors.
11) The medical device according to embodiment 10 wherein said sensor on said balloon catheter is selected from the group consisting of accelerometers, pressure sensors, contact sensors, position sensors, chemical microsensors, tissue metabolic sensors, mechanical stress sensors and temperature sensors.
12) The medical device according to embodiment 11 wherein said accelerometer detects acceleration, tilt, vibration, shock and or rotation.
13) The heart valve according to any one of embodiments 1 to 9 or medical device according to any one of embodiments 11 or 12 further comprising:
an electronic processor positioned upon and/or inside the heart valve or medical device that is electrically coupled to sensors.
14) The heart valve or medical device according to embodiment 13 wherein the electric coupling is a wireless coupling.
15) The heart valve or medical device according to embodiment 13 further including:
a memory coupled to the electronic processor and positioned upon and/or inside the heart valve or medical device.
16) The heart valve or medical device according to any one of embodiments 1 to 15 wherein said sensor is a plurality of sensors which are positioned on or within said heart valve, medical device and/or kit at a density of greater than 1, 2, 3, 4, 5, 6, 7, 8, 9, 10 or 20 sensors per square centimeter.
17) The heart valve or medical device according to any one of embodiments 1 to 15 wherein said sensor is a plurality of sensors which are positioned on or within said heart valve, medical device and/or kit at a density of greater than 1, 2, 3, 4, 5, 6, 7, 8, 9, 10 or 20 sensors per cubic centimeter.
18) The heart valve or medical device to any one of embodiments 1 to 17 wherein said sensors are placed randomly within the heart valve or medical device.
19) The heart valve or medical device according to any one of embodiments 1 to 18 wherein the one or more of the sensors are placed at specific locations within the heart valve or medical device.
20) A method comprising:
obtaining data from a sensor positioned at a plurality of locations between on and/or within a heart valve or medical device according to any one of embodiments 1 to 19 of a subject;
    storing the data in a memory device located on or within the heart valve or medical device; and
    transferring the data from the memory to a location outside the heart valve or medical device.
21) A method according to embodiment 20, further comprising the step of analyzing said data.
22) A method for detecting and/or recording an event in a subject with a heart valve or medical device as provided in any one of embodiments 1 to 19, comprising the step of interrogating at a desired point in time the activity of one or more sensors within the heart valve or medical device, and recording said activity.
23) The method according to embodiment 22 wherein the step of interrogating is performed by a subject which has an implanted heart valve, and the step of recording is performed on a wearable device.
24) The method according to any one of embodiments 22, or 23, wherein said recording is provided to a health care provider.
25) A method for imaging a heart valve or medical device, comprising the steps of
    (a) detecting the location of one or more sensors of a heart valve or medical device according to any one of embodiments 1 to 19; and
    (b) visually displaying the location of said one or more sensors, such that an image of the heart valve or medical device is created.
26) The method according to embodiment 25 wherein the step of detecting occurs over time.
27) The method according to embodiment 25 or 26, wherein said visual display shows changes in the positions of said sensors over time, and/or changes in temperature of the sensors or surrounding tissue over time.
28) The method according to any one of embodiments 25 to 27 wherein said visual display is a three-dimensional image of said heart valve.
29) A method for inserting a heart valve or medical device into a subject, comprising the steps of
    (a) inserting a heart valve or medical device according to any one of embodiments 1 to 19 into a subject; and
    (b) imaging the placement of said heart valve or medical device according to the method of any one of embodiments 25 to 28.
30) A method for examining a heart valve or medical device according to any one of embodiments 1 to 19 which has been previously inserted into a patient, comprising the step of imaging the heart valve according to the method of any one of embodiments 25 to 28.
31) A method of monitoring a heart valve, medical device, or kit within a subject, comprising:
transmitting a wireless electrical signal from a location outside the body to a location inside the subject's body;
receiving the signal at a sensor positioned on a heart valve, medical device, or kit according to any one of embodiments 1 to 19 located inside the body;
powering the sensor using the received signal;
sensing data at the sensor; and
outputting the sensed data from the sensor to a receiving unit located outside of the body.
32) The method according to embodiment 31 wherein said receiving unit is a watch, wrist band, cell phone or glasses.
33) The method according to embodiments 31 or 32 wherein said receiving unit is located within a subject's residence or office.
34) The method according to embodiments any one of embodiments 31 to 33 wherein said sensed data is provided to a health care provider.
35) The method according to any one of embodiments 31 to 34 wherein said sensed data is posted to one or more websites.
36) A non-transitory computer-readable storage medium whose stored contents configure a computing system to perform a method, the method comprising:
identifying a subject, the identified subject having at least one wireless heart valve, medical device, or kit according to any one of embodiments 1 to 19, each wireless heart valve, medical device, or kit having one or more wireless sensors;
directing a wireless interrogation unit to collect sensor data from at least one of the respective one or more wireless sensors; and
receiving the collected sensor data.

37) The non-transitory computer-readable storage medium of embodiment 36 whose stored contents configure a computing system to perform a method, the method further comprising:
identifying a plurality of subjects, each identified subject having at least one wireless heart valve, medical device, or kit, each wireless heart valve, medical device, or kit having one or more wireless sensors;
directing a wireless interrogation unit associated with each identified subject to collect sensor data from at least one of the respective one or more wireless sensors;
receiving the collected sensor data; and
aggregating the collected sensor data.

38) The non-transitory computer-readable storage medium of embodiment 36 whose stored contents configure a computing system to perform a method, the method further comprising:
removing sensitive subject data from the collected sensor data; and
parsing the aggregated data according to a type of sensor.

39) The non-transitory computer-readable storage medium of embodiment 36 whose stored contents configure a computing system to perform a method, wherein directing the wireless interrogation unit includes directing a control unit associated with the wireless interrogation unit.

40) The non-transitory computer readable storage medium according to any one of embodiments 36 to 39, wherein said heart valve, medical device, or kit is an assembly according to any one of embodiments 1 to 19.

41) The storage medium according to any one of embodiments 36 to 40 wherein said collected sensor data is received on a watch, wrist band, cell phone or glasses.

42) The storage medium according to any one of embodiments 36 to 41 wherein said collected sensor data is received within a subject's residence or office.

43) The storage medium according to any one of embodiments 36 to 42 wherein said collected sensed data is provided to a health care provider.

44) The storage medium according to any one of embodiments 36 to 43 wherein said sensed data is posted to one or more websites.

45) The method according to any one of embodiments 31 to 35, or storage medium according to any one of embodiments 36 to 44, wherein said data is analyzed.

46) The method or storage medium according to embodiment 45 wherein said data is plotted to enable visualization of change over time.

47) The method or storage medium according to embodiments 45 or 46 wherein said data is plotted to provide a three-dimensional image.

48) A method for determining degradation of a heart valve, comprising the steps of a) providing to a body passageway of a subject a heart valve according to any one of embodiments 1 to 7 or 16 to 19, and b) detecting a change in a sensor, and thus determining degradation of the heart valve.

49) The method according to embodiment 48 wherein said sensor is capable of detecting one or more physiological and/or locational parameters.

50) The method according to embodiment 48 or 49 wherein said sensor detects contact, fluid flow, pressure and/or temperature.

51) The method according to any one of embodiments 48 to 50 wherein said sensor detects a location within the subject.

52) The method according to any one of embodiments 48 to 50 wherein said sensor moves and/or is eliminated by the body upon degradation of the heart valve.

53) The method according to any one of embodiments 48 to 52 wherein the step of detecting is a series of detections over time.

54) A method for determining an infection associated with a heart valve, comprising the steps of a) providing to a body passageway of a subject a heart valve according to any one of embodiments 1 to 19, wherein said heart valve comprises at least one temperature sensor and/or metabolic sensor, and b) detecting a change in said temperature sensor and/or metabolic sensor, and thus determining the presence of an infection.

55) The method according to embodiment 54 wherein the step of detecting is a series of detections over time.

56) The method according to embodiments 54 or 55 wherein said change is greater than a 1% change over the period of one hour.

57) The method according to embodiments 54 to 56 wherein said change is a continually increasing temperature and/or metabolic activity over the course of 4 hours.

The various embodiments described above can be combined to provide further embodiments. All of the U.S. patents, U.S. patent application publications, U.S. patent applications, foreign patents, foreign patent applications and non-patent publications referred to in this specification are incorporated herein by reference, in their entirety. Aspects of the embodiments can be modified, if necessary to employ concepts of the various patents, applications and publications to provide yet further embodiments.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A medical device, comprising
a percutaneous heart valve comprising:
   a support frame,
   a valve surrounded by the support frame, the value comprising a plurality of leaflets,
   one or more contact sensors on the support frame,
   one or more accelerometers on the support frame,
   one or more pressure sensors positioned within or upon a first side of at least one of the plurality of leaflets, and
a balloon catheter comprising:
   a balloon,
   one or more contact sensors on the balloon, and
   one or more accelerometers on the balloon.

2. The medical device according to claim 1, further comprising at least one additional sensor on the balloon selected from the group consisting of pressure sensors, position sensors, chemical microsensors, tissue metabolic sensors, mechanical stress sensors and temperature sensors.

3. The medical device according to claim 1 wherein each of the accelerometer on the support frame and the accelerometer on the balloon detects acceleration, tilt, vibration, shock and or rotation.

4. The medical device according to claim 1 further comprising:
an electronic processor positioned upon and/or inside the heart valve or balloon catheter, where the electronic processor is electrically coupled to each of the one or more contact sensors on the support frame, the one or more accelerometers on the support frame, the one or more pressure sensors positioned within or upon the first side of at least one of the plurality of leaflets, the one or more contact sensors on the balloon, and the one or more accelerometers on the balloon.

5. The medical device according to claim 4 wherein the electric coupling is a wireless coupling.

6. The medical device according to claim 4 further including:
a memory coupled to the electronic processor and positioned upon and/or inside the heart valve or balloon catheter.

7. The medical device according to claim 1 wherein:
the one or more contact sensors on the support frame and the one or more accelerometers on the support frame are positioned on the support frame at a density greater than 1, 2, 3, 4, 5, 6, 7, 8, 9, 10 or 20 sensors per square centimeter,
the one or more pressure sensors within or upon the first side of at least one of the plurality of leaflets are positioned on the leaflet at a density greater than 1, 2, 3, 4, 5, 6, 7, 8, 9, 10 or 20 sensors per square centimeter, and
the one or more contact sensors on the balloon and the one or more accelerometers on the balloon are positioned on the balloon at a density greater than 1, 2, 3, 4, 5, 6, 7, 8, 9, 10 or 20 sensors per square centimeter.

8. The medical device according to claim 1, further comprising at least one additional sensor on the support frame, the additional sensor selected from the group consisting of pressure sensors, position sensors, chemical microsensors, tissue metabolic sensors, mechanical stress sensors and temperature sensors.

9. The medical device according to claim 1, further comprising at least one additional sensor on one of the plurality of leaflets, the additional sensor selected from the group consisting of accelerometers, contact sensors, position sensors, chemical microsensors, tissue metabolic sensors, mechanical stress sensors and temperature sensors.

10. The medical device according to claim 1, wherein the balloon catheter further comprises a catheter that carries the balloon, and further comprising at least one additional sensor on the catheter, the additional sensor selected from the group consisting of accelerometers, pressure sensors, contact sensors, position sensors, chemical microsensors, tissue metabolic sensors, mechanical stress sensors and temperature sensors.

11. The medical device of claim 1, further comprising one or more pressure sensors positioned within or upon a second side of at least one of the plurality of leaflets, where the second side is opposite the first side.

12. A method comprising:
obtaining data from a sensor positioned at a plurality of locations between on and/or within a heart valve and/or balloon catheter according to claim 1 of a subject;
storing the data in a memory device located on or within the heart valve or balloon catheter; and
transferring the data from the memory to a location outside the heart valve or balloon catheter.

13. A method according to claim 12, further comprising the step of analyzing said data.

14. A method for detecting and/or recording an event in a subject with a medical device as provided in claim 1, comprising the step of interrogating at a desired point in time the activity of one or more sensors within the heart valve or balloon catheter, and recording said activity.

15. The method according to claim 14 wherein the step of interrogating is performed by a subject which has an implanted heart valve, and the step of recording is performed on a wearable device.

16. The method according to claim 14, wherein said recording is provided to a health care provider.

17. A method for imaging a medical device according to claim 1 that has been placed inside of a patient, comprising the steps of
(a) detecting the location of one or more sensors of the heart valve or balloon catheter; and
(b) visually displaying the location of said one or more sensors, such that an image of the medical device is created.

18. The method according to claim 17 wherein the step of detecting occurs over time.

19. The method according to claim 17 wherein said visual display shows changes in the positions of said sensors over time, and/or changes in temperature of the sensors or surrounding tissue over time.

20. A method for inserting a medical device into a subject, comprising the steps of
(a) inserting a medical device according to claim 1 into a subject; and
(b) imaging the placement of said medical device according to a method comprising (i) detecting the location of one or more sensors of the heart valve or the balloon catheter; and (ii) visually displaying the location of said one or more sensors, such that an image of the heart valve or balloon catheter is created.

21. A method of monitoring a medical device within a subject, comprising:
transmitting a wireless electrical signal from a location outside the body to a location inside the subject's body;
receiving the signal at a sensor positioned on a medical device according to claim 1 located inside the body;
powering the sensor using the received signal;
sensing data at the sensor; and
outputting the sensed data from the sensor to a receiving unit located outside of the body.

* * * * *